(12) United States Patent
Huard et al.

(10) Patent No.: US 10,526,412 B2
(45) Date of Patent: Jan. 7, 2020

(54) ANTI APRIL (A PROLIFERATION-INDUCING LIGAND) ANTIBODIES AND THEIR USES FOR THE PROGNOSIS AND/OR DIAGNOSIS OF CANCER

(71) Applicants: UNIVERSITE GRENOBLE ALPES, Saint Martin d'heres (FR); UNIVERSITE DE LAUSANNE, Lausanne-dorigny (CH)

(72) Inventors: Bertrand Huard, Grenoble (FR); Pascal Schneider, Lausanne (CH)

(73) Assignees: UNIVERSITE GRENOBLE ALPES, Saint Martin d'Heres (FR); UNIVERSITE DE LAUSANNE, Lausanne-Dorigny (CH)

( * ) Notice: Subject to any disclaimer, the term of this patent is extended or adjusted under 35 U.S.C. 154(b) by 0 days.

(21) Appl. No.: 15/543,751

(22) PCT Filed: Jan. 14, 2016

(86) PCT No.: PCT/EP2016/050703
§ 371 (c)(1),
(2) Date: Jul. 14, 2017

(87) PCT Pub. No.: WO2016/113368
PCT Pub. Date: Jul. 21, 2016

(65) Prior Publication Data
US 2017/0369582 A1    Dec. 28, 2017

(30) Foreign Application Priority Data
Jan. 15, 2015  (EP) ..................... 15151345

(51) Int. Cl.
| C07K 16/00 | (2006.01) |
| C07K 16/28 | (2006.01) |
| A61K 39/00 | (2006.01) |
| C07K 16/24 | (2006.01) |

(52) U.S. Cl.
CPC ......... *C07K 16/2875* (2013.01); *A61K 39/00* (2013.01); *C07K 16/241* (2013.01); *C07K 2317/34* (2013.01); *C07K 2319/30* (2013.01); *C07K 2319/32* (2013.01)

(58) Field of Classification Search
None
See application file for complete search history.

(56) References Cited

U.S. PATENT DOCUMENTS

2011/0143367 A1* 6/2011 Huard ............... C07K 16/2875
435/7.2

FOREIGN PATENT DOCUMENTS

| WO | 2007/039489 A1 | 4/2007 | |
| WO | 2010/100056 A2 | 9/2010 | |
| WO | WO2010/100056 | * 9/2010 | |
| WO | WO2010100056 A2 * | 9/2010 | ......... C07K 16/2875 |

OTHER PUBLICATIONS

Hahne, et al., "April, A New Ligand of the Tumor Necrosis Factor Family, Stimulates Tumor Cell Growth," J. Exp. Med., vol. 188, No. 6, 1998, pp. 1185-1190.
Planelles, et al., "The Expanding Role of APRIL in Cancer and Immunity," Curr. Mol. Med., vol. 8, No. 8, 2008, 51 pages.
Schwaller, et al., "Neutrophil-Derived APRIL Concentrated in Tumor Lesions by Proteoglycans Correlates with Human B-Cell Lymphoma Aggressiveness," Blood, vol. 109, No. 1, 2007, pp. 331-338.
"APRIL (Human) Monoclonal Antibody (Aprily-8)," Enzo Life Sciences, http://www.enzolifesciences.com/ALX-804-149/april-human-mab-aprily-8/, 2017, 2 pages.
"APRIL/TNFSFI3 Antibody (Aprily-8)," NBP1-97587, Product Datasheet, www.novusbio.com, 2016, 4 pages.
Swerdlow, et al., "WHO Classification of Tumours of Haematopoietic and Lymphoid Tissues," Fourth Edition, 2008, pp. 234, 262-264, 323-334.
MetaMorph Microscopy Automation and Image Analysis Software, Molecular Devices, https://www.moleculardevices.com/systems/metamorph-research-imaging/metamorph-microscopy-automation-and-image-analysis-software, 2017, 2 pages.
Marsters, et al., "Interaction of the TNF Homologues BLyS and APRIL with the TNF Receptor Homologues BCMA and TACI," Current Biology, vol. 10, No. 13, pp. 785-788.
"PET Scans in Patients with Diffuse Large B-Cell Lymphoma Receiving Rituximab, Cyclophosphamide, Doxorubicin, Vincristine, and Prednisone," Clinical Trials.gov, https://clinicaltrials.gov/ct2/show/NCT00544219, 2016, 5 pages.
Ingold, K., et al., "Identification of Proteoglycans as the APRIL-Specific Binding Partners," Journal of Experimental Medicine, vol. 201, No. 9, 2005, pp. 1375-1383.
International Search Report issued in Application No. PCT/EP2016/050703, dated May 2, 2016.
European Search Report issued in Application No. EP 15151345, dated Jul. 2, 2015.

* cited by examiner

*Primary Examiner* — Lei Yao
(74) *Attorney, Agent, or Firm* — Young & Thompson

(57) ABSTRACT

An antibody or a fragment thereof directed against an epitope including or being constituted by at least six contiguous amino acids in the SEQ ID NO: 1 or a conformational epitope comprising or being constituted by at least six amino acids of SEQ ID NO: 1 which are always in the order of the sequence, and its use for the prognosis and/or the diagnosis of a cancer.

12 Claims, 7 Drawing Sheets
Specification includes a Sequence Listing.

A

B

| Above threshold | Threshold | Below threshold |

A

B

ANTI APRIL (A PROLIFERATION-INDUCING LIGAND) ANTIBODIES AND THEIR USES FOR THE PROGNOSIS AND/OR DIAGNOSIS OF CANCER

The present invention relates to new antibodies and their use for the prognosis and/or the diagnosis of a cancer.

The tumor environment remains largely ill-defined and clinically underused. Indeed, tumoricidal agents acting directly on malignant cells constitute most of the current tumor therapies. However, it is well accepted that tumor cells are critically dependent on their environment to maximally develop.

A proliferation inducing ligand (APRIL) is the last member cloned from the tumor necrosis factor superfamily (Hahne M, Kataoka T, Schroter M, Hofmann K, Irmler M, Bodmer J L, Schneider P, Bomand T, Holler N, French L E, et al. APRIL, a new ligand of the tumor necrosis factor family, stimulates tumor cell growth. *J Exp Med.* 1998; 188(6): 1185-90).

APRIL is an inflammatory molecule produced by myeloid cells, and worldwide, independent investigations conclude for an immune role for APRIL on B-lymphocytes at the level of survival, proliferation and differentiation (Planelles L, Medema J P, Hahne M, and Hardenberg G. The expanding role of APRIL in cancer and immunity. *Curr Mol Med.* 2008; 8(8):829-44).

Thus, it has been highlighted a promoting role for APRIL in tumors originating from these B-lymphocytes, for example Diffuse Large B Cell Lymphoma (DLBCL).

DLBCL is the B-Cell Lymphoma showing the most drastic APRIL upregulation in lesions (Schwaller J, Schneider P, Mhawech-Fauceglia P, McKee T, Myit S, Matthes T, Tschopp J, Donze O, Le Gal F A, and Huard B. Neutrophil-derived APRIL concentrated in tumor lesions by proteoglycans correlates with human B-Cell Lymphoma aggressiveness. *Blood.* 2007; 109(1):331-8).

DLBCL is also the most common subtype of non-Hodgkin lymphoma (NHL) accounting for approximately 30% of all newly diagnosed cases and more than 80% of aggressive lymphomas. It is highly prevalent in the Caucasian population.

The gold standard treatment of DLBCL is constituted by an association of four chemotherapeutic drugs abbreviated as CHOP and a monoclonal antibody directed toward a surface tumor antigen, called Rituximab®. Therefore, this treatment (R-CHOP) only includes direct tumoricidal reagent. Despite this intensive regimen, there is still 40% of resistant DLBCL, indicating the need to improve the treatment.

Considering the promoting role of APRIL in tumors originating from these B-lymphocytes, antibodies against APRIL as biomarkers for early prognosis of lymphoma patients have been developed. For example, the international application PCT/EP2006/066625 describes the in vitro use of a combination of monoclonal antibody Aprily-2 and a polyclonal or monoclonal antibody against the stalk fragment of APRIL having the amino acid sequence GTGGPSQNGEGYP (SEQ ID NO: 15), which is the domain which stays associated to the cell membrane after furin cleavage This international application also described the specific combination of Aprily-2 and Stalk-1. Aprily-2 recognizes the C-terminal TNF homology domain of APRIL secreted upon furin cleavage. Stalk-1 is a polyclonal rabbit antiserum which recognizes the membrane-proximal sequence in APRIL extracellular domain. Thus, Aprily-2 is able to localize secreted APRIL, and the second antibody against the stalk fragment of APRIL having the amino acid sequence SEQ ID NO: 15 allows the reliable identification of cells producing APRIL in vitro, in human tissues.

However, the prognosis according to the method described the international application PCT/EP2006/066625 needs the use of two antibodies, which is more expensive and requires more time compared to a technique in which a single antibody is used.

Moreover, it has been observed by the Inventors that the Aprily-2 antibody gave unexpected signals in healthy tissues. This has been first observed in human kidney with a staining in epithelial cells from tubules. This staining is not specific to APRIL since it is also observed in tubular epithelial cells from kidney of APRIL-deficient mice. Such staining at the level of kidney epithelium is not seen with Aprily-6 and Aprily-8. Hence, the Aprily-2 antibody cross-reacts with another protein independent from APRIL. It has also been observed this Aprily-2 cross-reactivity in human breast and salivary glands.

The combinations described in the international application PCT/EP2006/066625 do not seem reliable because the antibody Aprily-2 can lead to cross-reactions in several organs, and because the antibody against the stalk fragment of APRIL as mentioned previously can lead to false-positive results (this has also been observed by the Inventors).

Antibodies against APRIL are also described in the international application PCT/EP2010/052254. These antibodies can be used for therapeutic purposes.

Thus, there is a need of new antibodies, and their use for the prognosis and/or diagnosis of a cancer which is more reliable than those of the prior art.

There is also a need of new antibodies, and their use for the prognosis and/or diagnosis of a cancer which is simplified, notably which is faster and cheaper.

That is why one of the aims of the present invention is to provide antibodies or fragments thereof for their use for the prognosis and/or the diagnosis of a cancer, the said use being more reliable and more simple than the use of prior art.

Another aim of the present invention is also to provide compositions containing such antibodies or fragments thereof for their use for the prognosis and/or the diagnosis of a cancer, the said use being more reliable and more simple than the use the prior art.

Another aim of the present invention is also to provide an in vitro and/or ex vivo use of such antibodies or fragments thereof for the prognosis and/or the diagnosis of a cancer, the said use being more reliable and more simple than the use of the prior art.

Finally, another aim of the present invention is also to provide new antibodies or fragments thereof directed against APRIL that allow such more reliable and faster use.

Thus, the present invention concerns an antibody or a fragment thereof directed against APRIL, for its use for the prognosis and/or the diagnosis of a cancer.

The present invention also concerns a composition comprising or consisting of at least one antibody or a fragment thereof directed against APRIL, for its use for the prognosis and/or the diagnosis of a cancer.

The present invention also concerns the in vitro and/or ex vivo use of an antibody or a fragment thereof directed against APRIL, for its use for the prognosis and/or the diagnosis of a cancer.

Finally, the present invention also concerns new antibodies or a fragment thereof directed against APRIL.

The present invention relies on the determination by the Inventors of the epitope recognized by Aprily-8, a known monoclonal antibody which recognizes Human APRIL.

The invention also relies on the unexpected experimental results according to which the antibody Aprily-8 can be used alone, which means without a polyclonal or monoclonal antibody against the stalk fragment of APRIL having the amino acid sequence GTGGPSQNGEGYP (SEQ ID NO: 15), notably without the antibody Stalk-1, for the prognosis and/or the diagnosis of a cancer, notably a lymphoma.

The invention also relies on the unexpected experimental results according to which antibodies or fragment thereof directed against the same epitope of Aprily-8 or a part of this epitope can also be used alone, without a polyclonal or monoclonal antibody against the stalk fragment of APRIL having the amino acid sequence GTGGPSQNGEGYP (SEQ ID NO: 15), for the prognosis and/or the diagnosis of a cancer, notably a lymphoma.

Thus, in a first embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, for its use for the prognosis and/or the diagnosis of a cancer.

An "antibody" means a large protein with a Y-shape produced by plasma cells that is used by the immune system to identify and neutralize an antigen. Each tip of the Y-shape of an antibody contains a paratope that is specific for one particular epitope on an antigen, allowing these two structures to bind together with precision.

A "epitope" or antigenic determinant, corresponds to the particular part of the antigen that is recognized by the antibody (more specifically by the parotope).

A "paratope" means the specific area of the antibody whose function is to recognize the antigen.

An antibody is an assembly of two dimers, each consisting of a heavy chain and a light chain. Each of the heavy and light chain comprises a constant region and a variable region. The assembly of the chains that comprise an antibody permits to define the structure characterized by the Y-shape, where:
the base of the Y corresponds to the Fc constant region that is recognized by complement and Fc receptors, and
the end of the arms of the Y correspond to the respective assembly of the variable regions of the light chain variable and heavy chain.

The variable regions consists of three domains determining antigen recognition (CDR, also called the hypervariable regions) surrounded by four structural domains (FR regions).

An antibody according to the present invention can be a chimeric antibody or a humanised antibody.

A "chimeric antibody" is an antibody whose sequences of the variable regions of the light chains and heavy chains belong to a species different from the sequences of the constant regions of the light chains and heavy chains.

A "humanized antibody" refers to an antibody whose all or part of the sequences of the hypervariable regions and sometimes some amino acids of the FR regions (regions Framework) belong to sequences of non-human origin while the sequences of the constant regions and variable regions not involved in antigen recognition are of human origin.

A "fragment" means any portion of an antibody that retains the ability to bind to the epitope recognized by the full length antibody. Examples of fragments include, but are not limited to, Fab, Fab' and F(ab')$_2$, Fd, single-chain Fvs (scFv), single-chain antibodies, disulfide-linked Fvs (dsFv) and fragments comprising either a VL or VH region. Epitope-binding fragments, including single-chain antibodies, may comprise the variable region(s) alone or in combination with the entirety or a portion of the following: hinge region, CH1, CH2, and CH3 domains.

Such fragments may contain one or both Fab fragments or the F(ab')$_2$ fragment. Further, the fragments may be or may combine members of any one of the following immunoglobulin classes: IgG, IgM, IgA, IgD, or IgE, and the subclasses thereof.

Fab and F(ab')$_2$ fragments may be produced by proteolytic cleavage, using enzymes such as papain (Fab fragments) or pepsin (F(ab')$_2$ fragments).

The "single-chain FVs" ("scFvs") fragments are epitope-binding fragments that contain at least one fragment of an antibody heavy chain variable region (V$_H$) linked to at least one fragment of an antibody light chain variable region (V$_L$). The linker may be a short, flexible peptide selected to assure that the proper three-dimensional folding of the V$_L$ and V$_H$ regions occurs once they are linked so as to maintain the target molecule binding-specificity of the whole antibody from which the single-chain antibody fragment is derived. The carboxyl terminus of the V$_L$ or V$_H$ sequence may be covalently linked by a linker to the amino acid terminus of a complementary V$_L$ or V$_H$ sequence.

Single-chain antibody fragments of the present invention contain amino acid sequences having at least one of the variable or complementarity determining regions (CDRs) of the whole antibodies described in this specification, but lack some or all of the constant domains of those antibodies.

The expression "six contiguous amino acids" means six amino acids which are immediately next to each other in SEQ ID NO: 1. Thus, an "epitope comprising or being constituted by at least six contiguous amino acids in the SEQ ID NO: 1" corresponds to a linear epitope by opposition to a conformational epitope.

The expression "at least six" means also at least seven, eight, nine, ten, eleven, twelve, thirteen, fourteen, fifteen, sixteen, seventeen, or eighteen (the full-length of SEQ ID NO: 1).

A "conformational epitope" means an epitope which is formed by amino acids which are not contiguous in SEQ ID NO: 1. This means that the amino acids are not immediately next to each other in SEQ ID NO: 1. However, some of the amino acids can be immediately next to each other, and thus a conformational epitope according to the present invention can contain only one amino acid which is not contiguous to the others in SEQ ID NO: 1.

SEQ ID NO: 1 is the following sequence in amino acids: TFTMGQWSREGQGRQET. It includes the epitope recognized by Aprily-8, which has been determined in the present invention. Aprily-8 is a monoclonal antibody which recognizes Human APRIL and which is commercially available, at Enzo Life Sciences, enzolifesciences.com.

APRIL is a transmembrane protein undergoing a cleavage by a furin protease in order to be secreted. Full length APRIL is not detectable in tissues because of a rapid and efficient cleavage by furin proteases (Schwaller et al., Blood 2007).

SEQ ID NO: 16 is the complete sequence of APRIL protein. SEQ ID NO: 16 is as follows:

```
MGGPVREPALSVALWLSWGAALGAVACAMALLTQQTELQSLRREVS

RLQGTGGPSQNGEGYPWQSLPEQSSDALEAWENGERSRKRRAVLTQ
```

-continued
KQKKQHSVLHLVPINATSKDDSDVTEVMWQPALRRGRGLQAQGYGV

RIQDAGVYLLYSQVLFQDV<u>TFTMGQVVSREGQGRQET</u>LFRCIRSMP

SHPDRAYNSCYSAGVFHLHQGDILSVIIPRARAKLNLSPHGTFLGF

VKL.

The underlined part corresponds to SEQ ID NO: 1.

Furin protease cleaves before the Alanine at position 88 (from position 1 which is the initiating methionine). Thus, secreted APRIL is from amino acid 88 (an alanine) to amino acid 233 (a leucine) and APRIL part remaining anchored at the membrane after furin processing is from amino acid 1 (a methionine) to amino acid 87 (an arginine).

The expression "which are always in the order of the said sequence" means that even if the amino acids representing the sequence of the conformational epitope are not contiguous, their order is limited by the one of SEQ ID NO: 1. Notably, TFMSGQET (SEQ ID NO: 17) can be an example of a sequence of a conformational epitope according to the present invention because this order of amino acids can be found in the SEQ ID NO: 1 (TFTMGQVVSREGQGRQET or TFTMGQVVSREGQGRQET). On the contrary, TFGEQVV (SEQ ID NO: 18) cannot be an example of a sequence of a conformational epitope according to the present invention because this order of amino acids cannot be found in the SEQ ID NO: 1.

A "prognosis" is the prospect of survival and recovery from a disease as anticipated from the usual course of that disease or indicated by special features (signs, symptoms, . . . ) of the case.

A "diagnosis" is the identification of a disease from its signs and symptoms.

A cancer means also a malignant tumor or malignant neoplasm.

In another embodiment, the present invention relates to an antibody or a fragment thereof directed against an epitope comprising or being constituted by at least six contiguous amino acids in the SEQ ID NO: 1, as mentioned above, for its use for the prognosis and/or the diagnosis of a cancer.

In another embodiment, the present invention relates to an antibody or a fragment thereof directed against a conformational epitope comprising or being constituted by at least six amino acids of SEQ ID NO: 1 which are always in the order of the said sequence, as mentioned above, for its use for the prognosis and/or the diagnosis of a cancer.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein said epitope comprises or is constituted by at least one of the following sequences:

TFTMGQ (SEQ ID NO: 2)

FTMGQV (SEQ ID NO: 3)

TMGQVV (SEQ ID NO: 4)

MGQVVS (SEQ ID NO: 5)

GQVVSR (SEQ ID NO: 6)

QVVSRE (SEQ ID NO: 7)

VVSREG (SEQ ID NO: 8)

VSREGQ (SEQ ID NO: 9)

SREGQG (SEQ ID NO: 10)

REGQGR (SEQ ID NO: 11)

EGQGRQ (SEQ ID NO: 12)

GQGRQE (SEQ ID NO: 13)

QGRQET (SEQ ID NO: 14)

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is monoclonal or polyclonal.

A monoclonal antibody is an antibody coming from only one type of cell, the hybridoma cell. A hybridoma cell is a cell fusion which will continually produce antibodies. It is produced in vitro by the fusion of a single B-lymphocyte that produces antibodies and a myeloma tumor cell.

A polyclonal antibody is an antibody derived from a pool of B-lymphocytes.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis of a cancer.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the diagnosis of a cancer.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and the diagnosis of a cancer.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-8.

As previously mentioned, Aprily-8 is a monoclonal antibody which recognizes Human APRIL, whose the epitope is included in the SEQ ID NO: 1 and which is commercially available, at Enzo Life Sciences, enzolifesciences.com, or at Novus Biological, under the reference NBP1-97587.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis of a cancer, wherein the said antibody is Aprily-8.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the diagnosis of a cancer, wherein the said antibody is Aprily-8.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and the diagnosis of a cancer, wherein the said antibody is Aprily-8.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-6.

The said antibody Aprily-6 is notably produced by the hybridoma which has been deposited at the "Collection Nationale de Cultures de Microorganismes" (CNCM, Institut Pasteur, 25 rue du Docteur Roux, F-75724 PARIS Cedex 15, France) on Dec. 16, 2014, under the number CNCM I-4929.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis of a cancer, wherein the said antibody is Aprily-6.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the diagnosis of a cancer, wherein the said antibody is Aprily-6.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and the diagnosis of a cancer, wherein the said antibody is Aprily-6.

In a preferred embodiment, the antibodies or fragment thereof according to the present invention are used without the antibody Stalk-1, and/or without polyclonal or monoclonal antibody directed against the stalk fragment of APRIL having the said amino acid sequence of SEQ ID NO: 15.

In other word, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is used without the antibody Stalk-1, and/or without polyclonal or monoclonal antibody directed against the stalk fragment of APRIL having the said amino acid sequence of SEQ ID NO: 15.

In another embodiment, the presents invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-8, and wherein the said antibody is used without the antibody Stalk-1, and/or without polyclonal or monoclonal antibody directed against the stalk fragment of APRIL having the said amino acid sequence of SEQ ID NO: 15.

In another embodiment, the presents invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-6, and wherein the said antibody is used without the antibody Stalk-1, and/or without polyclonal or monoclonal antibody directed against the stalk fragment of APRIL having the said amino acid sequence of SEQ ID NO: 15.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said cancer is a lymphoma or a solid tumor, such as glioblastoma or colorectal cancer.

A "solid tumor" means an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas.

In a preferred embodiment, the present invention concerns solid tumors which are malignant.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said lymphoma is chosen among all types of Hodgkin lymphomas, among the Burkitt lymphoma and Diffuse Large B-Cell Lymphoma types.

Hodgkin lymphoma is a type of lymphoma, which is a cancer originating from white blood cells called lymphocytes. The WHO classification puts Hodgkin lymphoma into two main groups, which are:

Classical types
Nodular lymphocyte predominant type

There are four types of classical Hodgkin lymphoma. All these types contain abnormal cells called Reed-Sternberg cells that can be seen under the microscope. Reed-Sternberg cells are a type of white blood cell (B lymphocyte) that has become cancerous. They are larger than the normal lymphocytes and usually have two nuclei. The four types of classical Hodgkin lymphoma are:

Nodular sclerosing
Mixed cellularity
Lymphocyte rich
Lymphocyte depleted

The Nodular lymphocyte predominant type is more common in older people but can occur in young people. The main difference between this type and classical Hodgkin lymphoma is that in the nodular lymphocyte predominant type there are very few Reed-Sternberg cells. But there are other abnormal cells. This type of Hodgkin lymphoma is often only in one group of lymph nodes when it is diagnosed (localised disease).

Complete informations about the Hodgkin lymphomas can be found in the textbook WHO classification of tumours of hematopoietic and lymphoid tissues (WHO press, 4$^{th}$ edition, 2008).

Burkitt lymphoma (BL) is a cancer of the lymphatic system, particularly of B lymphocytes found in the germinal center. There are three different types of Burkitt lymphoma:

Endemic BL
Sporadic BL
Immunodeficiency-associated BL

More information about the Burkitt lymphomas can be found in the textbook WHO classification of tumours of hematopoietic and lymphoid tissues (WHO press, 4$^{th}$ edition, 2008).

Diffuse Large B-Cell Lymphoma (DLBCL) is the most aggressive type of non-Hodgkin lymphoma, and probably the more variable in terms of subtypes identified. Pathological examination revealed many subtypes as already stated in 2008 in the textbook WHO classification of tumours of hematopoietic and lymphoid tissues (WHO press, 4$^{th}$ edition, 2008). DLBCL heterogeneity has started to be molecularly defined with the Germinal Center, Activated B cells, and undefined subtypes.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said lymphoma is Diffuse Large B-Cell Lymphoma types.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said prognosis is the risk assessment for patients newly diagnosed for a B-Cell Lymphoma, notably for a Diffuse Large B-Cell Lymphoma types.

The expression "risk assessment" means the risk that the patient has to dye of this cancer.

The expression "newly diagnosed for a B-Cell Lymphoma" means that the patient did not receive any treatment for its lymphoma (a B-Cell Lymphoma). Its B-Cell Lymphoma has just been discovered.

The expression "newly diagnosed for a Diffuse Large B-Cell Lymphoma types" means the patient did not receive any treatment for its lymphoma (Diffuse Large B-Cell Lymphoma types). Its Diffuse Large B-Cell Lymphoma has just been discovered.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said diagnosis is an improved subtyping of B-Cell Lymphomas, notably for the Diffuse Large B-Cell Lymphoma types.

It is now recognized that the single clinical entity under the name Diffuse Large B-Cell Lymphoma is in fact constituted by subtypes varying in their capacity to respond to current treatments, warranting the identification of biomarker(s) allowing an improved subtyping" to adjust the treatment.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said prognosis is the risk assessment for patients newly diagnosed for a B-Cell Lymphoma, notably for a Diffuse Large B-Cell Lymphoma types, and wherein the said diagnosis is an improved subtyping of B-Cell Lymphomas, notably for the Diffuse Large B-Cell Lymphoma types.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of cancer in high risk patient.

The expression "high risk patients" means persons at high risk to dye of their cancer.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of cancer, wherein the high risk patient has a number of cells positive for secreted APRIL equal or superior to 45 positive cells per 0.12 mm$^2$.

The expression "45 positive cells per 0.12 mm$^2$" means a ratio of 45 positive cells per 0.12 mm$^2$ and is not a limitative value. In other words, if the area of the biopsy is 0.24 mm$^2$, the high risk patient has a number of cells positive for secreted APRIL equal or superior to 90 positive cells.

In other words, the ratio between the number of cells positive for secreted APRIL and the area of the biopsy (in mm$^2$) is 375 (45/0.12).

Consequently, and in a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of cancer, wherein the high risk patient has a ratio between the number of cells positive for secreted APRIL and the area of the biopsy in mm$^2$ equal or superior to 375 cells/mm$^2$.

In a preferred embodiment, the number of cells positive for secreted APRIL is determined in a biopsy from any kind of organs for the said patient.

In a preferred embodiment, the number of cells positive for secreted APRIL is determined thanks to Aprily-6 staining or Aprily-8 staining.

Aprily-6 staining or Aprily-8 staining can be determined as follows:
Staining for secreted APRIL,
Numbering of positives cells on a determined area.

The expression <<positive cells for secreted APRIL>> means that the antibody Aprily-6 or Aprily-8 binds to the biopsy of the patient, because the said biopsy contains tumor cells binding secreted APRIL.

The term "mm$^2$" corresponds to the area of the biopsy.

In a preferred embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the high risk patient has a APRIL value above the reference threshold sample previously calculated at 4.6 10$^4$ according to the Metamorph microscopy automation and image analysis software.

Thus, to determine a high risk patient for the prognosis and/or the diagnosis of lymphoma, the number of cells cited above (45 positive cells per 0.12 mm$^2$) can be used, but also the APRIL value above the reference threshold sample previously calculated at 4.6 10$^4$ according to the Metamorph microscopy automation and image analysis software.

More information about the Metamorph microscopy automation and image analysis software can be found at moleculardevices.com.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is used with the antibody Aprily-2.

As mentioned in the international application PCT/EP2006/066625, the monoclonal antibody Aprily-2 is produced by a hybridoma cell which has been deposited at the CNCM, on Sep. 23, 2005, under the number I-3500. CNCM means the Collection Nationale de Culture des Microorganismes which is located at Institut Pasteur, 25 rue du Docteur Roux, F-75725 Paris Cedex 15.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-8, and wherein the said antibody is used with the antibody Aprily-2.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-6, and wherein the said antibody is used with the antibody Aprily-2.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the antibody is Aprily-8, and wherein the said antibody is used with Aprily-6.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the antibody is Aprily-8, and wherein the said antibody is used with Aprily-6 and Aprily-2.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein antibody is Aprily-8 which is used with Aprily-6, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the antibody is Aprily-8 which is used with Aprily-6 and Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the antibody is Aprily-8 which is used with Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the antibody is Aprily-6 which is used with Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is attached with a radioactive label or with any kind of labeling enabling non-invasive imaging.

For example, the said antibody can be labelled with a compound like a radionucleide, a fluorochrome, or an enzyme.

The particular label or detectable group used does not significantly interfere with the specific binding of the antibody used in the assay. The detectable group can be any material having a detectable physical or chemical property.

A label is any composition detectable by spectroscopic, photochemical, biochemical, immunochemical, electrical, optical, radiological or chemical means. The label may be coupled directly or indirectly to the desired component of the assay according to methods well known in the art. As indicated above, a wide variety of labels may be used, with the choice of label depending on the sensitivity required, the ease of conjugation with the compound, stability requirements, the available instrumentation and disposal provisions.

Generally, a ligand molecule (for example biotin) is covalently bound to the antibody. The ligand then binds to an anti-ligand (for example streptavidin) molecule, which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, a haptenic or antigenic compound can be used in combination with an antibody.

The antibodies can also be conjugated directly to signal-generating compounds, for example, by conjugation with an enzyme or fluorophore. Enzymes of interest as labels will primarily be hydrolases, particularly phosphatases, esterases and glycosidases, or oxidoreductases, particularly peroxidases.

Fluorescent compounds include fluorescein and its derivatives, rhodamine and its derivatives, dansyl, umbelliferone, . . . . Chemiluminescent compounds include luciferin, and 2,3-dihydrophtalazinediones, for example, luminol. Means for detecting labels are well known in the art. Thus, for example, where the label is a radioactive label, means for detection include a scintillation counter or photographic film as in autoradiography. Where the label is a fluorescent label, it may be detected by exciting the fluorophore with the appropriate wavelength of light and detecting the resulting fluorescence. The fluorescence may be detected visually, by means of a photographic film, by the use of electronic detectors such as charge coupled devices (CCDs) or photomultipliers and the like.

Similarly, enzyme labels may be detected by providing the appropriate substrates for the enzyme and detecting the resulting reaction product. Finally simple colorimetric labels may be detected simply by observing the color associated with the label.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is used in combination with an antibody directed against a tumor cell marker, such as an antibody directed against CD20, or an antibody directed against a B-cell marker, such as an antibody directed against CD19, CD21 or CD22.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody does not block the binding of APRIL to its receptor TACI and/or BCMA.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said conformational epitope is not an epitope of SEQ ID NO: 44 (VSREGQGRQ), optionally supported by SEQ ID NO: 2 (TFTMGQ).

The expression "the said conformational epitope is not an epitope of SEQ ID NO: 44 (VSREGQGRQ), optionally supported by SEQ ID NO: 2 (TFTMGQ)" means that the said conformational epitope is not an epitope of SEQ ID NO: 44, nor a conformational epitope comprising or constituted by SEQ ID NO: 44 and SEQ ID NO: 2.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said conformational epitope is not an epitope of SEQ ID NO: 45 (SMPSHP), optionally supported by SEQ ID NO: 46 (TLFR) and/or SEQ ID NO: 47 (QDVTFTMGQ).

The expression "the said conformational epitope is not an epitope of SEQ ID NO: 45 (SMPSHP), optionally supported by SEQ ID NO: 46 (TLFR) and/or SEQ ID NO: 47 (QDVT-FTMGQ)" means that the said conformational epitope is not an epitope of SEQ ID NO: 45 (or IRSMPSHPDRA of SEQ ID NO: 48), nor a conformational epitope comprising or constituted by:
SEQ ID NO: 45 and SEQ ID NO: 46, or
SEQ ID NO: 45 and SEQ ID NO: 47, or
SEQ ID NO: 45 and SEQ ID NO: 46 and SEQ ID NO: 47.

In a second embodiment, the present invention relates to a composition comprising or consisting of at least an antibody or a fragment thereof for its use as mentioned above.

The composition of the invention may be administered systemically or topically in a physiologic buffer such as PBS or NaCl 0.9%.

Thus, in another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, for its use for the prognosis and/or the diagnosis of a cancer.

In another embodiment, the present invention relates to a composition comprising or consisting of at least an antibody or a fragment thereof directed against an epitope comprising or being constituted by at least six contiguous amino acids in the SEQ ID NO: 1, as mentioned above, for its use for the prognosis and/or the diagnosis of a cancer.

In another embodiment, the present invention relates to a composition comprising or consisting of at least an antibody or a fragment thereof directed against a conformational epitope comprising or being constituted by at least six amino acids of SEQ ID NO: 1 which are always in the order of the said sequence, as mentioned above, for its use for the prognosis and/or the diagnosis of a cancer.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein said epitope comprises or is constituted by at least one of the following sequences:

```
TFTMGQ        (SEQ ID NO: 2)

FTMGQV        (SEQ ID NO: 3)

TMGQVV        (SEQ ID NO: 4)

MGQVVS        (SEQ ID NO: 5)

GQVVSR        (SEQ ID NO: 6)

QVVSRE        (SEQ ID NO: 7)

VVSREG        (SEQ ID NO: 8)

VSREGQ        (SEQ ID NO: 9)

SREGQG        (SEQ ID NO: 10)

REGQGR        (SEQ ID NO: 11)

EGQGRQ        (SEQ ID NO: 12)

GQGRQE        (SEQ ID NO: 13)

QGRQET        (SEQ ID NO: 14)
```

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is monoclonal or polyclonal.

In another embodiment, the present invention relates to a composition comprising or consisting at least of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis of a cancer.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the diagnosis of a cancer.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and the diagnosis of a cancer.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-8.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis of a cancer, wherein the said antibody is Aprily-8.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the diagnosis of a cancer, wherein the said antibody is Aprily-8.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and the diagnosis of a cancer, wherein the said antibody is Aprily-8.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-6.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis of a cancer, wherein the said antibody is Aprily-6.

In another embodiment, the present invention relates to a composition comprising or consisting of at least an antibody or a fragment thereof directed against an epitope comprising or being constituted by at least six contiguous amino acids in the SEQ ID NO: 1 which are always in the order of the said sequence, as mentioned above, for its use for the diagnosis of a cancer, wherein the said antibody is Aprily-6.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and the diagnosis of a cancer, wherein the said antibody is Aprily-6.

In a preferred embodiment, the present invention relates to a composition comprising or consisting of at least an antibody or a fragment thereof according to the present invention which are used without the antibody Stalk-1, and/or without polyclonal or monoclonal antibody directed against the stalk fragment of APRIL having the amino acid sequence of SEQ ID NO: 15.

In other word, the present invention also relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is used without the antibody Stalk-1, and/or without polyclonal or monoclonal antibody directed against the stalk fragment of APRIL having the amino acid sequence of SEQ ID NO: 15.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-8, and wherein the said antibody is used without the antibody Stalk-1, and/or without polyclonal or monoclonal antibody directed against the stalk fragment of APRIL having the amino acid sequence of SEQ ID NO: 15.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-6, and wherein the said antibody is used without the antibody Stalk-1, and/or without polyclonal or monoclonal antibody directed against the stalk fragment of APRIL having the amino acid sequence of SEQ ID NO: 15.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said cancer is lymphoma or a solid tumor, such as glioblastoma or colorectal cancer.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said lymphoma is chosen among all types of Hodgkin lymphomas, among the Burkitt lymphoma and Diffuse Large B-Cell Lymphoma types.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said lymphoma is Diffuse Large B-Cell Lymphoma types.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said prognosis is the risk assessment for patients newly diagnosed for a B-Cell Lymphoma, notably for a Diffuse Large B-Cell Lymphoma types.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said diagnosis is an improved subtyping of B-Cell Lymphomas, notably for the Diffuse Large B-Cell Lymphoma types.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of lymphoma, wherein the said prognosis is the risk assessment for patients newly diagnosed for a B-Cell Lymphoma, notably for a Diffuse Large B-Cell Lymphoma types, and wherein the said diagnosis is an improved subtyping of B-Cell Lymphomas, notably for the Diffuse Large B-Cell Lymphoma types.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, in high risk patient.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, for its use for the prognosis and/or the diagnosis of lymphoma, wherein the high risk patient has a APRIL value above the reference threshold sample previously calculated at $4.6 \cdot 10^4$ according to the Metamorph microscopy automation and image analysis software.

In a preferred embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of cancer, wherein the high risk patient has a number of cells positive for secreted APRIL equal or superior to 45 positive cells per $0.12 \text{ mm}^2$.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is used with the antibody Aprily-2.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-8, and wherein the said antibody is used with the antibody Aprily-2.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is Aprily-6, and wherein the said antibody is used with the antibody Aprily-2.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the composition comprises or consists of an antibody Aprily-8, and an antibody Aprily-6.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the composition comprises or consists of an antibody Aprily-8, an antibody Aprily-6, and an antibody Aprily-2.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the composition comprises or consists of an antibody Aprily-8, an antibody Aprily-6, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the composition comprises or consists of an antibody Aprily-8, an antibody Aprily-6, an antibody Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the composition comprises or consists of an antibody Aprily-8, an antibody Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the composition comprises or consists of an antibody Aprily-6, an antibody Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is attached with a radioactive label or with any kind of labeling enabling non-invasive imaging.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody is used in combination with an antibody directed against a tumor cell marker, such as an antibody directed against CD20, or an antibody directed against a B-cell marker, such as an antibody directed against CD19, CD21 or CD22.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said antibody does not block the binding of APRIL to its receptor TACI and/or BCMA.

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said conformational epitope is not an epitope of SEQ ID NO: 44 (VS-REGQGRQ), optionally supported by SEQ ID NO: 2 (TFT-MGQ).

In another embodiment, the present invention relates to a composition comprising or consisting of at least an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, as mentioned above, for its use for the prognosis and/or the diagnosis of a cancer, wherein the said conformational epitope is not an epitope of SEQ ID NO: 45 (SMPSHP), optionally supported by SEQ ID NO: 46 (TLFR) and/or SEQ ID NO: 47 (QDVTFTMGQ).

In a third embodiment, the present invention also concerns the in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, for the prognosis and/or the diagnosis of a cancer.

In this embodiment, the present invention relates to an in vitro and/or ex vivo use of an antibody or a fragment thereof directed against an epitope comprising or being constituted by at least six contiguous amino acids in the SEQ ID NO: 1, or of a composition comprising or containing the said antibody or fragment thereof, as mentioned above, for the prognosis and/or the diagnosis of a cancer.

In another embodiment, the present invention relates to an in vitro and/or ex vivo use of an antibody or a fragment thereof directed against a conformational epitope comprising or being constituted by at least six amino acids of SEQ ID NO: 1 which are always in the order of the said sequence, or of a composition comprising or containing the said antibody or fragment thereof as mentioned above, for the prognosis and/or the diagnosis of a cancer.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein said epitope comprises or is constituted by at least one of the following sequences:

| Sequence | |
|---|---|
| TFTMGQ | (SEQ ID NO: 2) |
| FTMGQV | (SEQ ID NO: 3) |
| TMGQVV | (SEQ ID NO: 4) |
| MGQVVS | (SEQ ID NO: 5) |
| GQVVSR | (SEQ ID NO: 6) |
| QVVSRE | (SEQ ID NO: 7) |
| VVSREG | (SEQ ID NO: 8) |
| VSREGQ | (SEQ ID NO: 9) |
| SREGQG | (SEQ ID NO: 10) |
| REGQGR | (SEQ ID NO: 11) |
| EGQGRQ | (SEQ ID NO: 12) |
| GQGRQE | (SEQ ID NO: 13) |
| QGRQET | (SEQ ID NO: 14) |

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is monoclonal or polyclonal.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and the diagnosis of a cancer.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis of a cancer.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the diagnosis of a cancer.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-8.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and the diagnosis of a cancer, wherein the said antibody is Aprily-8.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis of a cancer, wherein the said antibody is Aprily-8.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the diagnosis of a cancer, wherein the said antibody is Aprily-8.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-6.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and the diagnosis of a cancer, wherein the said antibody is Aprily-6.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis of a cancer, wherein the said antibody is Aprily-6.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and the diagnosis of a cancer, wherein the said antibody is Aprily-6.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof as mentioned above, for the prognosis and/or the diagnosis of a cancer, wherein the said antibody is used without the antibody Stalk-1, and/or without polyclonal or monoclonal antibody directed against the stalk fragment of APRIL having the said amino acid sequence of SEQ ID NO: 15.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-8, and wherein the said antibody is used without the antibody Stalk-1, and/or without polyclonal or monoclonal antibody directed against the stalk fragment of APRIL having the said amino acid sequence of SEQ ID NO: 15.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-6, and wherein the said antibody is used to without the antibody Stalk-1, and/or without polyclonal or monoclonal antibody directed against the stalk fragment of APRIL having the said amino acid sequence of SEQ ID NO: 15.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the antibody is Aprily-8 which is used with Aprily-6.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the antibody is Aprily-8 which is used with Aprily-6 and Aprily-2.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the antibody is Aprily-8 which is used with Aprily-6, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the antibody is Aprily-8 which is used with Aprily-6 and Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein antibody is Aprily-8 which is used with Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the antibody is Aprily-6 which is used with Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said cancer is lymphoma or a solid tumor, such as glioblastoma or colorectal cancer.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the said lymphoma is chosen among all types of Hodgkin lymphomas, among the Burkitt lymphoma and Diffuse Large B-Cell Lymphoma types.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the said lymphoma is Diffuse Large B-Cell Lymphoma types.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the said prognosis is the risk assessment for patients newly diagnosed for a B-Cell Lymphoma, notably for a Diffuse Large B-Cell Lymphoma types.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the said diagnosis is an improved subtyping of B-Cell Lymphomas, notably for the Diffuse Large B-Cell Lymphoma types.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the said prognosis is the risk assessment for patients newly diagnosed for a B-Cell Lymphoma, notably for a Diffuse Large B-Cell Lymphoma types, and wherein the said diagnosis is an improved subtyping of B-Cell Lymphomas, notably for the Diffuse Large B-Cell Lymphoma types.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, in a biological sample from high risk patient.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the high risk patient has a APRIL value above the reference threshold sample previously calculated at 4.6 $10^4$ according to the Metamorph microscopy automation and image analysis software.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of lymphoma, wherein the high risk patient has a number of cells positive for secreted APRIL equal or superior to 45 positive cells per 0.12 mm$^2$.

In a preferred embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said biological sample is chosen among biopsies, notably biopsies of B-Cell Lymphoma patients when the cancer is a lymphoma.

A "biopsy" means a very small part of a pathologic organ or tissue harvested from the patient for a diagnostic purpose. B-cell lymphomas are usually developing in lymphoid organs. But biopsies for B-cell lymphoma may also originate from other organs such as the central nervous system, the intestine and the skin.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is used at a concentration from 0.1 to 500 µg/ml, notably from 1 to 100 µg/ml, particularly from 1 to 50 µg/ml, and more particularly from 1 to 15 µg/ml.

The expression "from 0.1 to 500 µg/ml" means notably 0.1; 0.2; 0.3; 0.4; 0.5; 0.6; 0.7; 0.8; 0.9; 200; 250; 300; 350; 400; 450 and 500 µg/ml. It means also close values such as 0.09 µg/ml or 500.1 µg/ml.

The expression "from 1 to 100 µg/ml" means notably 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99 and 100 µg/ml. It means also close values such as 0.99 µg/ml or 100.1 µg/ml.

The expression "from 1 to 50 µg/ml" means notably 1; 1.5; 2; 2.5; 3; 3.5; 4; 4.5; 5; 5.5; 6; 6.5; 7; 7.5; 8; 8.5; 9, 9.5; 10; 10.5; 11; 11.5; 12; 12.5; 13; 13.5; 14; 14.5; 15; 15.5; 16; 16.5; 17; 17.5; 18; 18.5; 19; 19.5; 20; 20.5; 21; 21.5; 22; 22.5; 23; 23.5; 24; 24.5; 25; 25.5; 26; 26.5; 27; 27.5; 28; 28.5; 29; 29.5; 30; 30.5; 31; 31.5; 32; 32.5; 33; 33.5; 34; 34.5; 35; 35.5; 36; 36.5; 37; 37.5; 38; 38.5; 39; 39.5; 40; 40.5; 41; 41.5; 42; 42.5; 43; 43.5; 44; 44.5; 45; 45.5; 46; 46.5; 47; 47.5; 48; 48.5; 49; 49.5 and 50 µg/ml. It means also close values such as 0.99 µg/ml or 50.1 µg/ml.

The expression "from 1 to 15 µg/ml" means notably 1; 1.5; 2; 2.5; 3; 3.5; 4; 4.5; 5; 5.5; 6; 6.5; 7; 7.5; 8; 8.5; 9; 9.5; 10; 10.5; 11; 11.5; 12; 12.5; 13; 13.5; 14; 14.5 and 15 µg/ml. It means also close values such as 0.99 µg/ml or 15.1 µg/ml.

A preferred range of concentration is from 2.5 to 50 µg/ml, notably the use of Aprily-8 at a concentration between 2.5 to 50 µg/ml because the obtained signal will be quantified.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-8, and wherein the said antibody is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-6, and wherein the said antibody is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is used with the antibody Aprily-2.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-8, and wherein the said antibody is used with the antibody Aprily-2.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-6, and wherein the said antibody is used with the antibody Aprily-2.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer wherein the said antibody is used at a concentration from 0.1 to 500 µg/ml, notably from 1 to 100 µg/ml, particularly from 1 to 50 µg/ml, and more particularly from 1 to 15 µg/ml, and wherein the antibody Aprily-2 is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-8 which is used at a concentration from 0.1 to 500 µg/ml, notably from 1 to 100 µg/ml, particularly from 1 to 50 µg/ml, and more particularly from 1 to 15 µg/ml, and wherein the antibody Aprily-2 is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is Aprily-6 and which is used at a concentration from 0.1 to 500 µg/ml, notably from 1 to 100 µg/ml, particularly from 1 to 50 µg/ml, and more particularly from 1 to 15 µg/ml and wherein the antibody Aprily-2 is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is attached with a radioactive label or with any kind of labeling enabling non-invasive imaging.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody is used in combination with an antibody directed against a tumor cell marker, such as an antibody directed against CD20, or an antibody directed against a B-cell marker, such as an antibody directed against CD19, CD21 or CD22.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said antibody does not block the binding of APRIL to its receptor TACI and/or BCMA.

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said conformational epitope is not an epitope of SEQ ID NO: 44 (VSREGQGRQ), optionally supported by SEQ ID NO: 2 (TFTMGQ).

In another embodiment, the present invention relates to an in vitro and/or ex vivo use of an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, or of a composition comprising or containing the said antibody or fragment thereof, as mentioned above, for the prognosis and/or the diagnosis of a cancer, wherein the said conformational epitope is not an epitope of SEQ ID NO: 45 (SMPSHP), optionally supported by SEQ ID NO: 46 (TLFR) and/or SEQ ID NO: 47 (QDVTFTMGQ).

In a fourth embodiment, the present invention relates to an in vitro and/or ex vivo method for the prognosis and/or the diagnosis and/or the risk assessment of a cancer, the said method using an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence.

In a preferred embodiment, the present invention relates to an in vitro and/or ex vivo method for the risk assessment of a cancer. It permits to determine the state of the severity disease.

In another embodiment, the present invention relates to an in vitro and/or ex vivo method for the prognosis and/or the diagnosis and/or the risk assessment of a cancer, the said method using an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, and the said method comprising the following step:
  detecting in a biological sample, of a patient affected or suspected to be affected by said cancer, a number of cells positive for secreted APRIL.

In another embodiment, the present invention relates to an in vitro and/or ex vivo method for the prognosis and/or the diagnosis and/or the risk assessment of a cancer, the said method using an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, and the said method comprising the following steps:
  detecting in a biological sample, of a patient affected or suspected to be affected by said cancer, a number of cells positive for secreted APRIL,
  comparing the said number with the value of 45 positive cells for secreted APRIL per 0.12 mm$^2$,
  deducing from said comparison whether the said patient may expect suffering from a cancer.

If the patient has a number of cells positive for secreted APRIL, which is equal or superior to 45 positive cells per 0.12 mm$^2$, the said patient is identified as a high risk patient for the development of a cancer, notably a B-Cell Lymphoma. This patient is also identified as eligible for antagonist treatment for APRIL. Such antagonist treatment for APRIL can be a monoclonal antibody blocking the binding of APRIL to its receptors as described in the international application WO2010/100056, or a soluble form of one of its receptor such as ATACICEPT (UNique Ingredient Identifier (UNII): K3D9A0ICQ3).

If the patient has a number of cells positive for secreted APRIL, which is inferior to 45 positive cells per 0.12 mm$^2$, the said patient is not identified as a high risk patient for the development of a cancer, notably a B-Cell Lymphoma.

If the patient has a number of cells positive for secreted APRIL, which is inferior to 45 positive cells per 0.12 mm$^2$, but which is very close to this value, for example 44.9 positive cells per 0.12 mm$^2$, the said patient is identified as a patient with a low risk.

In another embodiment, the present invention relates to an in vitro and/or ex vivo method for the prognosis and/or the diagnosis and/or the risk assessment of a cancer, the said method using an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, and the said method comprising the following steps:
  marking a biological sample, of a patient affected or suspected to be affected by said cancer, with at least one of the antibodies according to the present invention, notably Aprily-8 or Aprily-6,
  detecting in the said biological sample, of a patient affected or suspected to be affected by said disease, a number of cells positive for secreted APRIL,
  comparing the said number with the value of 45 positive cells for secreted APRIL per 0.12 mm$^2$,
  deducing from said comparison whether said patient may expect suffering from a cancer.

In another embodiment, the present invention relates to an in vitro and/or ex vivo method for the prognosis and/or the diagnosis and/or the risk assessment of a cancer, as mentioned above, wherein the said epitope comprises or is constituted by at least one of the following sequences:

| | |
|---|---|
| TFTMGQ | (SEQ ID NO: 2) |
| FTMGQV | (SEQ ID NO: 3) |
| TMGQVV | (SEQ ID NO: 4) |
| MGQVVS | (SEQ ID NO: 5) |
| GQVVSR | (SEQ ID NO: 6) |
| QVVSRE | (SEQ ID NO: 7) |
| VVSREG | (SEQ ID NO: 8) |
| VSREGQ | (SEQ ID NO: 9) |
| SREGQG | (SEQ ID NO: 10) |
| REGQGR | (SEQ ID NO: 11) |
| EGQGRQ | (SEQ ID NO: 12) |
| GQGRQE | (SEQ ID NO: 13) |
| QGRQET | (SEQ ID NO: 14) |

In another embodiment, the present invention relates to an in vitro and/or ex vivo method for the prognosis and/or the diagnosis and/or the risk assessment of a cancer, as mentioned above, wherein the said antibody is monoclonal or polyclonal.

In another embodiment, the present invention relates to an in vitro and/or ex vivo method for the prognosis and/or the diagnosis and/or the risk assessment of a cancer, as mentioned above, wherein the said antibody is Aprily-8.

In another embodiment, the present invention relates to an in vitro and/or ex vivo method for the prognosis and/or the diagnosis and/or the risk assessment of a cancer, as mentioned above, wherein the said antibody is Aprily-6.

In another embodiment, the present invention relates to an in vitro and/or ex vivo method for the prognosis and/or the diagnosis and/or the risk assessment of a cancer, as mentioned above, wherein the said method does not use the antibody Stalk-1 and/or a polyclonal or monoclonal antibody directed against the stalk fragment of APRIL having the amino acid sequence of SEQ ID NO: 15.

In another embodiment, the present invention relates to an in vitro and/or ex vivo method for the prognosis and/or the diagnosis and/or the risk assessment of a cancer, as mentioned above, wherein the said method uses the antibody Aprily-8, and does not use the antibody Stalk-1 and/or a polyclonal or monoclonal antibody directed against the stalk fragment of APRIL having the amino acid sequence of SEQ ID NO: 15.

In another embodiment, the present invention relates to an in vitro and/or ex vivo method for the prognosis and/or the diagnosis and/or the risk assessment of a cancer, as mentioned above, wherein the said method uses the antibody Aprily-6, and does not use the antibody Stalk-1 and/or a polyclonal or monoclonal antibody directed against the stalk fragment of APRIL having the amino acid sequence of SEQ ID NO: 15.

In another embodiment, the present invention relates to an in vitro and/or ex vivo method for the prognosis and/or the diagnosis and/or the risk assessment of a cancer, as mentioned above, wherein the said cancer is lymphoma or a solid tumor, such as glioblastoma or colorectal cancer.

In another embodiment, the present invention relates to an in vitro and/or ex vivo method for the prognosis and/or the diagnosis and/or the risk assessment of a cancer, as mentioned above, wherein the said lymphoma is chosen among all types of Hodgkin lymphomas, among the Burkitt lymphoma and Diffuse Large B-Cell Lymphoma types.

In another embodiment, the present invention relates to an in vitro and/or ex vivo method for the prognosis and/or the diagnosis and/or the risk assessment of a cancer, as mentioned above, wherein the said lymphoma is Diffuse Large B-Cell Lymphoma types.

In another embodiment, the present invention relates to an in vitro and/or ex vivo method for the prognosis and/or the diagnosis and/or the risk assessment of a cancer, as mentioned above, wherein the said prognosis is the risk assessment for patients newly diagnosed for a B-Cell Lymphoma, notably for a Diffuse Large B-Cell Lymphoma types.

In another embodiment, the present invention relates to an in vitro and/or ex vivo method for the prognosis and/or the diagnosis and/or the risk assessment of a cancer, as mentioned above, wherein the said diagnosis is an improved subtyping of B-Cell Lymphomas, notably for the Diffuse Large B-Cell Lymphoma types.

In another embodiment, the present invention relates to an in vitro and/or ex vivo method for the prognosis and/or the diagnosis and/or the risk assessment of a cancer, as mentioned above, wherein the said prognosis is the risk assessment for patients newly diagnosed for a B-Cell Lymphoma, notably for a Diffuse Large B-Cell Lymphoma types, and wherein the said diagnosis is an improved subtyping of B-Cell Lymphomas, notably for the Diffuse Large B-Cell Lymphoma types.

In another embodiment, the present invention relates to an in vitro and/or ex vivo method for the prognosis and/or the diagnosis and/or the risk assessment of a cancer, as mentioned above, wherein the said biological sample is a biological sample of a high risk patient.

In another embodiment, the present invention relates to an in vitro and/or ex vivo method for the prognosis and/or the diagnosis and/or the risk assessment of a cancer, as mentioned above, wherein the high risk patient has a number of cells positive for secreted APRIL equal or superior to 45 positive cells per 0.12 mm$^2$ in its biopsy.

In another embodiment, the present invention relates to an in vitro and/or ex vivo method for the prognosis and/or the diagnosis and/or the risk assessment of a cancer, as mentioned above, wherein the high risk patient has a APRIL value above the reference threshold sample previously calculated at 4.6 10$^4$ according to the Metamorph microscopy automation and image analysis software, when the cancer is a Diffuse Large B-Cell Lymphoma types.

In another embodiment, the present invention relates to an in vitro and/or ex vivo method for the prognosis and/or the diagnosis and/or the risk assessment of a cancer, as mentioned above, wherein the said antibody is used with the antibody Aprily-2.

In another embodiment, the present invention relates to an in vitro and/or ex vivo method for the prognosis and/or the diagnosis and/or the risk assessment of a cancer, as mentioned above, wherein the said antibody is Aprily-8, and wherein the said antibody is used with the antibody Aprily-2.

In another embodiment, the present invention relates to an in vitro and/or ex vivo method for the prognosis and/or the diagnosis and/or the risk assessment of a cancer, as mentioned above, wherein the said antibody is Aprily-6, and wherein the said antibody is used with the antibody Aprily-2.

In another embodiment, the present invention relates to an in vitro and/or ex vivo method for the prognosis and/or the diagnosis and/or the risk assessment of a cancer, as mentioned above, wherein the said biological sample is chosen among biopsies, notably biopsies of B-Cell Lymphoma patients when the cancer is a lymphoma.

In another embodiment, the present invention relates to an in vitro and/or ex vivo method for the prognosis and/or the diagnosis and/or the risk assessment of a cancer, as mentioned above wherein the said antibody is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo method for the prognosis and/or the diagnosis and/or the risk assessment of a cancer, as mentioned above wherein the said antibody is Aprily-8, and wherein the said antibody is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo method for the prognosis and/or the diagnosis and/or the risk assessment of a cancer, as mentioned above, wherein the said antibody is Aprily-6, and wherein the said antibody is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo method for the prognosis and/or the diagnosis and/or the risk assessment of a cancer, as mentioned above, wherein the said antibody is used at a concentration from 0.1 to 500 µg/ml, notably from 1 to 100 µg/ml, particularly from 1 to 50 µg/ml, and more particularly from 1 to µg/ml, and wherein the antibody Aprily-2 is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo method for the prognosis and/or the diagnosis and/or the risk assessment of a cancer, as mentioned above, wherein the said antibody is Aprily-8 which is used at a concentration from 0.1 to 500 µg/ml, notably from 1 to 100 µg/ml, particularly from 1 to 50 µg/ml, and more particularly from 1 to 15 µg/ml, and wherein the antibody Aprily-2 is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo method for the prognosis and/or the diagnosis and/or the risk assessment of a cancer, as mentioned above, wherein the said antibody is Aprily-6 which is used at a concentration from 0.1 to 500 µg/ml, notably from 1 to 100 µg/ml, particularly from 1 to 50 µg/ml, and more particularly from 1 to 15 µg/ml and wherein the antibody Aprily-2 is used at a concentration from 0.1 to 500 µg/ml, notably from 1 to 100 µg/ml, particularly from 1 to 50 µg/ml, and more particularly from 1 to 15 µg/ml.

In another embodiment, the present invention relates to an in vitro and/or ex vivo method for the prognosis and/or the diagnosis and/or the risk assessment of a cancer, as mentioned above, wherein the antibody is Aprily-8, and wherein the said antibody is used with Aprily-6.

In another embodiment, the present invention relates to an in vitro and/or ex vivo method for the prognosis and/or the diagnosis and/or the risk assessment of a cancer, as mentioned above, wherein the antibody is Aprily-8, and wherein the said antibody is used with Aprily-6 and Aprily-2.

In another embodiment, the present invention relates to an in vitro and/or ex vivo method for the prognosis and/or the diagnosis and/or the risk assessment of a cancer, as mentioned above, wherein the antibody is Aprily-8 which is used with Aprily-6, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an in vitro and/or ex vivo method for the prognosis and/or the diagnosis and/or the risk assessment of a cancer, as mentioned above, wherein the antibody is Aprily-8 which is used with Aprily-6 and Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention relates to an in vitro and/or ex vivo method for the prognosis and/or the diagnosis and/or the risk assessment of a cancer, as mentioned above, wherein the antibody is Aprily-8 which is used with Aprily-2, with the proviso that the antibody Stalk-1 is excluded, and/or with the proviso that a polyclonal or monoclonal antibody directed against the stalk fragment of APRIL having the amino acid sequence of SEQ ID NO: 15 is excluded.

In another embodiment, the present invention relates to an in vitro and/or ex vivo method for the prognosis and/or the diagnosis and/or the risk assessment of a cancer, as mentioned above, wherein the antibody is Aprily-6 which is used with Aprily-2, with the proviso that the antibody Stalk-1 is excluded, and/or with the proviso that a polyclonal or monoclonal antibody directed against the stalk fragment of APRIL having the amino acid sequence of SEQ ID NO: 15 is excluded.

In another embodiment, the present invention relates to an in vitro and/or ex vivo method for the prognosis and/or the diagnosis and/or the risk assessment of a cancer, as mentioned above, wherein the said antibody is attached with a radioactive label or with any kind of labeling enabling non-invasive imaging.

In another embodiment, the present invention relates to an in vitro and/or ex vivo method for the prognosis and/or the diagnosis and/or the risk assessment of a cancer, as mentioned above, wherein the said antibody is used in combination with an antibody directed against a tumor cell marker, such as an antibody directed against CD20, or an antibody directed against a B-cell marker, such as an antibody directed against CD19, CD21 or CD22.

In another embodiment, the present invention relates to an in vitro and/or ex vivo method for the prognosis and/or the diagnosis and/or the risk assessment of a cancer, as mentioned above, wherein the said antibody does not block the binding of APRIL to its receptor TACI and/or BCMA.

In another embodiment, the present invention relates to an in vitro and/or ex vivo method for the prognosis and/or the diagnosis and/or the risk assessment of a cancer, as mentioned above, wherein the said conformational epitope is not an epitope of SEQ ID NO: 44 (VSREGQGRQ), optionally supported by SEQ ID NO: 2 (TFTMGQ).

In another embodiment, the present invention relates to an in vitro and/or ex vivo method for the prognosis and/or the diagnosis and/or the risk assessment of a cancer, as mentioned above, wherein the said conformational epitope is not an epitope of SEQ ID NO: 45 (SMPSHP), optionally supported by SEQ ID NO: 46 (TLFR) and/or SEQ ID NO: 47 (QDVTFTMGQ).

In a fifth embodiment, the present invention also concerns a kit for the prognosis and/or the diagnosis of a cancer comprising at least one antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence.

In another embodiment, the present invention also concerns a kit for the prognosis and/or the diagnosis of a cancer, as mentioned above, wherein the said epitope comprises or is constituted by at least one of the following sequences:

```
                          (SEQ ID NO: 2)
           TFTMGQ (SEQ ID NO: 3)
           FTMGQV (SEQ ID NO: 4)
           TMGQVV (SEQ ID NO: 5)
           MGQVVS (SEQ ID NO: 6)
           GQVVSR (SEQ ID NO: 7)
           QVVSRE (SEQ ID NO: 8)
           VVSREG (SEQ ID NO: 9)
           VSREGQ
```

-continued

SREGQG (SEQ ID NO: 10)

REGQGR (SEQ ID NO: 11)

EGQGRQ (SEQ ID NO: 12)

GQGRQE (SEQ ID NO: 13)

QGRQET (SEQ ID NO: 14)

In another embodiment, the present invention also concerns a kit for the prognosis and/or the diagnosis of a cancer, as mentioned above, wherein the said antibody is monoclonal or polyclonal.

In another embodiment, the present invention also concerns a kit for the prognosis and/or the diagnosis of a cancer, as mentioned above, wherein the said antibody is Aprily-8.

In another embodiment, the present invention also concerns a kit for the prognosis and/or the diagnosis of a cancer, as mentioned above, wherein the said antibody is Aprily-6.

In another embodiment, the present invention also concerns a kit for the prognosis and/or the diagnosis of a cancer, as mentioned above, wherein the kit does not contain the antibody Stalk-1, and/or a polyclonal or monoclonal antibody directed against the stalk fragment of APRIL having the said amino acid sequence of SEQ ID NO: 15.

In another embodiment, the present invention also concerns a kit for the prognosis and/or the diagnosis of a cancer, as mentioned above wherein the kit contains the antibody Aprily-8, and wherein the kit does not contain the antibody Stalk-1, and/or a polyclonal or monoclonal antibody directed against the stalk fragment of APRIL having the said amino acid sequence of SEQ ID NO: 15.

In another embodiment, the present invention also concerns a kit for the prognosis and/or the diagnosis of a cancer, as mentioned above wherein the kit contains the antibody Aprily-6, and wherein the kit does not contain the antibody Stalk-1, and/or a polyclonal or monoclonal antibody directed against the stalk fragment of APRIL having the said amino acid sequence of SEQ ID NO: 15.

In another embodiment, the present invention also concerns a kit for the prognosis and/or the diagnosis of a cancer, as mentioned above, wherein the kit also contains the antibody Aprily-2.

In another embodiment, the present invention also concerns a kit for the prognosis and/or the diagnosis of a cancer, as mentioned above, wherein the kit contains the antibody Aprily-8, and wherein the kit also contains the antibody Aprily-2.

In another embodiment, the present invention also concerns a kit for the prognosis and/or the diagnosis of a cancer, as mentioned above, wherein the kit contains the antibody Aprily-6, and wherein the kit also contains the antibody Aprily-2.

In another embodiment, the present invention also concerns a kit for the prognosis and/or the diagnosis of a cancer, as mentioned above, wherein the kit contains the antibody Aprily-8, and wherein the kit also contains the antibody Aprily-6.

In another embodiment, the present invention also concerns a kit for the prognosis and/or the diagnosis of a cancer, as mentioned above, wherein the kit contains the antibody Aprily-8, and wherein the kit also contains the antibody Aprily-6, and the antibody Aprily-2.

In another embodiment, the present invention also concerns a kit for the prognosis and/or the diagnosis of a cancer, as mentioned above, wherein the kit contains the antibody Aprily-8, and wherein the kit also contains the antibody Aprily-6, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention also concerns a kit for the prognosis and/or the diagnosis of a cancer, as mentioned above, wherein the kit contains the antibody Aprily-8, and wherein the kit also contains the antibody Aprily-6, and the antibody Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention also concerns a kit for the prognosis and/or the diagnosis of a cancer, as mentioned above, wherein the kit contains the antibody Aprily-8, and wherein the kit also contains the antibody Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention also concerns a kit for the prognosis and/or the diagnosis of a cancer, as mentioned above, wherein the kit contains the antibody Aprily-6, and wherein the kit also contains the antibody Aprily-2, with the proviso that the antibody Stalk-1 is excluded, and/or with the proviso that polyclonal or monoclonal antibody directed against the stalk fragment of APRIL having the amino acid sequence of SEQ ID NO: 15 is excluded.

In another embodiment, the present invention also concerns a kit for the prognosis and/or the diagnosis of a cancer, as mentioned above, wherein the said antibody is used in combination with an antibody directed against a tumor cell marker, such as an antibody directed against CD20, or an antibody directed against a B-cell marker, such as an antibody directed against CD19, CD21 or CD22.

In another embodiment, the present invention also concerns a kit for the prognosis and/or the diagnosis of a cancer, as mentioned above, wherein the said antibody does not block the binding of APRIL to its receptor TACI and/or BCMA.

In another embodiment, the present invention also concerns a kit for the prognosis and/or the diagnosis of a cancer, as mentioned above, wherein the said conformational epitope is not an epitope of SEQ ID NO: 44 (VS-REGQGRQ), optionally supported by SEQ ID NO: 2 (TFT-MGQ).

In another embodiment, the present invention also concerns a kit for the prognosis and/or the diagnosis of a cancer, as mentioned above, wherein the said conformational epitope is not an epitope of SEQ ID NO: 45 (SMPSHP), optionally supported by SEQ ID NO: 46 (TLFR) and/or SEQ ID NO: 47 (QDVTFTMGQ).

In a sixth embodiment, the present invention also relates to an antibody, notably monoclonal or polyclonal, which is susceptible to bind specifically to the specific sequence recognized by the monoclonal antibody secreted by the hydridoma which has been deposited at the Collection Nationale de Cultures de Microorganismes on Dec. 16, 2014, under the number CNCM I-4929, with the proviso that the antibody Aprily-8 is excluded.

In another embodiment, the present invention relates to an antibody, notably monoclonal or polyclonal, which is susceptible to bind specifically to the specific sequence recognized by the monoclonal antibody secreted by the hydridoma which has been deposited at the Collection Nationale de Cultures de Microorganismes on Dec. 16, 2014, under the number CNCM I-4929, and which does not block the binding of APRIL to its receptor TACI and/or BCMA, with the proviso that the antibody Aprily-8 is excluded.

APRIL has two canonical signaling receptors, the B-cell maturation antigen (BCMA) and the transmembrane activator and CAML interactor (TACI), almost exclusively expressed by B cells (see Marsters, S. A. et al. Interaction of the TNF homologues BLyS and APRIL with the TNF receptor homologues BCMA and/or TACI. *Curr Biol* 10, 785-788 (2000), for more information on BCMA and TACI).

The expression "which does not block the binding of APRIL to its receptor TACI and/or BCMA" means that the antibodies according to the present invention do not block the binding of APRIL to its receptor TACI. This also means that the antibodies according to the present invention do not block the binding of APRIL to its receptor BCMA. This also means that the antibodies according to the present invention do not block the binding of APRIL to its receptor TACI and the binding of APRIL to its receptor BCMA.

The antibodies according to the present invention do not block the binding of APRIL to its receptor TACI and/or BCMA. This means that the antibodies according to the present invention cannot be used for therapeutic purposes, notably in diseases in which APRIL has a promoting role.

The expression "specific sequence" means an epitope comprising or being constituted by at least six contiguous amino acids in the SEQ ID NO: 1 or a conformational epitope comprising or being constituted by at least six amino acids of SEQ ID NO: 1 which are always in the order of the said sequence.

In other words, this antibody binds to an epitope which is essentially similar to the epitope of the antibody which itself is obtainable from the hydridoma which has been deposited at the Collection Nationale de Cultures de Microorganismes on Dec. 16, 2014, under the number CNCM I-4929.

In other words, this antibody binds to the same epitope as the antibody which itself is obtainable from the hydridoma which has been deposited at the Collection Nationale de Cultures de Microorganismes on Dec. 16, 2014, under the number CNCM I-4929.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, with the proviso that the antibody Aprily-8 is excluded.

In another embodiment, the present invention relates to an antibody, notably monoclonal or polyclonal, or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, and which does not block the binding of APRIL to its receptor TACI and/or BCMA, with the proviso that the antibody Aprily-8 is excluded.

In another embodiment, the present invention relates to an antibody or a fragment thereof directed against an epitope comprising or being constituted by at least six contiguous amino acids in the SEQ ID NO: 1, wherein the said antibody is monoclonal or polyclonal, and notably wherein the said antibody does not block the binding of APRIL to its receptor TACI and/or BCMA.

In another embodiment, the present invention relates to an antibody or a fragment thereof directed against a conformational epitope comprising or being constituted by at least six amino acids of SEQ ID NO: 1 which are always in the order of the said sequence, wherein the said antibody is monoclonal or polyclonal, and notably wherein the said antibody does not block the binding of APRIL to its receptor TACI and/or BCMA.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, wherein said epitope comprises or is constituted by at least one of the following sequences:

| | |
|---|---|
| TFTMGQ | (SEQ ID NO: 2) |
| FTMGQV | (SEQ ID NO: 3) |
| TMGQVV | (SEQ ID NO: 4) |
| MGQVVS | (SEQ ID NO: 5) |
| GQVVSR | (SEQ ID NO: 6) |
| QVVSRE | (SEQ ID NO: 7) |
| VVSREG | (SEQ ID NO: 8) |
| VSREGQ | (SEQ ID NO: 9) |
| SREGQG | (SEQ ID NO: 10) |
| REGQGR | (SEQ ID NO: 11) |
| EGQGRQ | (SEQ ID NO: 12) |
| GQGRQE | (SEQ ID NO: 13) |
| QGRQET | (SEQ ID NO: 14) |

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, wherein said epitope comprises or is constituted by at least one of the following sequences:

SEQ ID NO: 2, or
SEQ ID NO: 3, or
SEQ ID NO: 4, or
SEQ ID NO: 5, or
SEQ ID NO: 6, or
SEQ ID NO: 7, or
SEQ ID NO: 8, or
SEQ ID NO: 9, or
SEQ ID NO: 10, or
SEQ ID NO: 11, or
SEQ ID NO: 12, or
SEQ ID NO: 13, or
SEQ ID NO: 14,
and wherein the said antibody does not block the binding of APRIL to its receptor TACI and/or BCMA.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, wherein the said antibody is monoclonal or polyclonal, and notably wherein the said antibody does not block the binding of APRIL to its receptor TACI and/or BCMA.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, wherein the said antibody is Aprily-6, and notably wherein the said antibody does not block the binding of APRIL to its receptor TACI and/or BCMA.

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, wherein the said conformational epitope is not an epitope of SEQ ID NO: 44 (VSREGQGRQ), optionally supported by SEQ ID NO: 2 (TFTMGQ).

In another embodiment, the present invention relates to an antibody or a fragment thereof directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, wherein the said conformational epitope is not an epitope of SEQ ID NO: 45 (SMPSHP), optionally supported by SEQ ID NO: 46 (TLFR) and/or SEQ ID NO: 47 (QDVTFTMGQ).

In another embodiment, the present invention relates to a hydridoma producing a monoclonal antibody Aprily-6 as mentioned above, wherein the said hydridoma has been deposited at the "Collection Nationale de Cultures de Microorganismes" (CNCM, Institut Pasteur, 25 rue du Docteur Roux, F-75724 PARIS Cedex 15, France) on Dec. 16, 2014, under the number CNCM I-4929.

The antibody according to the present invention can also be produced according to the methods described as follows.

For example, Aprily-6 is generated in mice or rat by immunization with recombinant soluble human APRIL (aa88-233) and fusing immunized splenocytes with the immortalized mouse myeloma cell line Sp2/0 (ATCC CRL-15810). Hybridoma supernatants are then screened for their reactivity in ELISA with the coated immunogen.

The antibody according to the invention can also be produced by the phage-display method. This involves selecting the antibody sequences having the desired antigenic specificity, from a library of immunoglobulin sequences, by using a system of type Display (e.g. phage display) and by using an antigen.

The antibody according to the invention can also be produced by injection of the appropriate antigen (for example human APRIL) into an animal, with recovery of the produced antibody in the serum of the said animal.

The present invention is illustrated by the following Figures and Examples, which do not limit the scope of the invention.

The parts A and C represent the results in color and the parts B, and D represent the result in black and white.

In parts A and B, the first and the second column correspond to healthy kidneys from human patients and APRIL-deficient mouse, respectively.

The first line corresponds to the immunostaining with a control isotype-matched mouse IgG1 (cIg) (2 µg/ml).

The second line corresponds to the immunostaining with the antibody Aprily-2, (2 µg/ml).

The third line corresponds to the immunostaining with the antibody Aprily-6, (10 µg/ml).

The fourth line corresponds to the immunostaining with the antibody Aprily-8, (2 µg/ml).

In parts C and D, the first and the second column correspond to healthy breast and salivary glands from human patients, respectively.

The first line corresponds to the immunostaining with a control isotype-matched mouse IgG1 (cIg) (2 µg/ml).

The second line corresponds to the immunostaining with the antibody Aprily-2, (2 µg/ml). The cross-reactivity of Aprily-2 on epithelial cells is arrowed.

The third line corresponds to the immunostaining with the antibody Aprily-6, (10 µg/ml).

Figure 2:
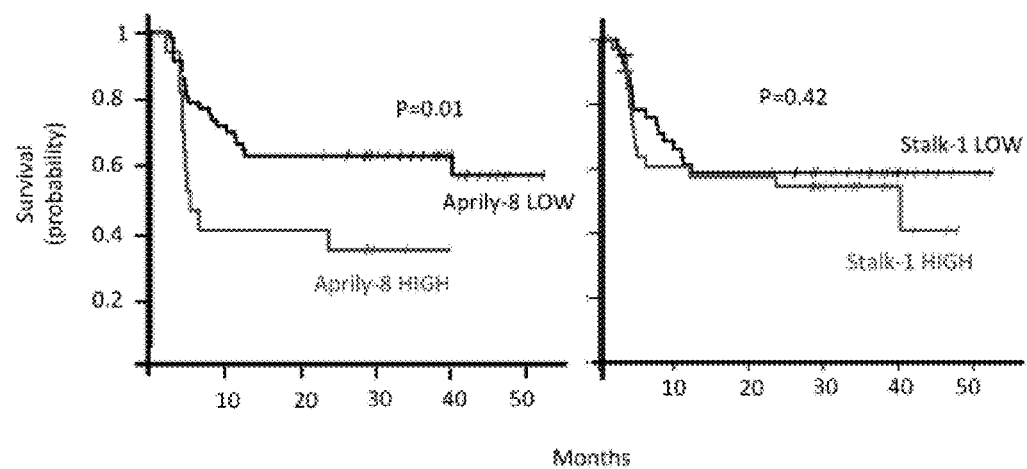
Figure 2:
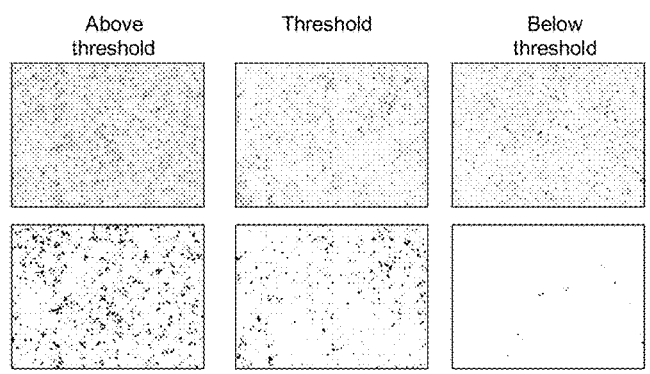

FIG. 2 represents the prospective survival study for DLBCL patients stratified according to APRIL (secreted form and APRIL-producing cells) expression.

Part A shows the Kaplan-Meyer analysis, and statistical analysis based on a Log-rank test was performed. A p-value equal or inferior to 0.05 is considered significant.

Abscissa shows the months and the ordinate axis shows the probability of survival.

The left panel shows the probability of survival, from lifetime data, according to the staining by Aprily-8 of secreted APRIL.

The right panel shows the probability of survival, from lifetime data, according to the staining by Stalk-1 of infiltrating cells producing APRIL.

The term «Aprily-8 LOW» means a low concentration of APRIL, which means a value inferior to the threshold value of $4.6 \cdot 10^4$ according to the Metamorph microscopy automation and image analysis software.

The term «Aprily-8 HIGH» means a high concentration of APRIL, which means a value equal or superior to the threshold value of $4.6 \cdot 10^4$ according to the Metamorph microscopy automation and image analysis software.

The term «Stalk-1 LOW» means a low number of APRIL-producing cells, which means a value inferior to 49 per 0.12 mm².

The term «Stalk-1 HIGH» means a high number of APRIL-producing cells, which means a value equal or superior to 49 per 0.12 mm².

The distinction between «Stalk-1 LOW» and «Stalk-1 HIGH» is not really important because no value of Stalk-1 permits to identify two groups of patients with different survival.

Part B shows representative color (upper panel) and black and white (bottom panel) pictures for biopsies below, equal (threshold) and above the threshold value for Aprily-8 (the threshold value being $4.6 \cdot 10^4$ according to the Metamorph microscopy automation and image analysis software).

Figure 3:
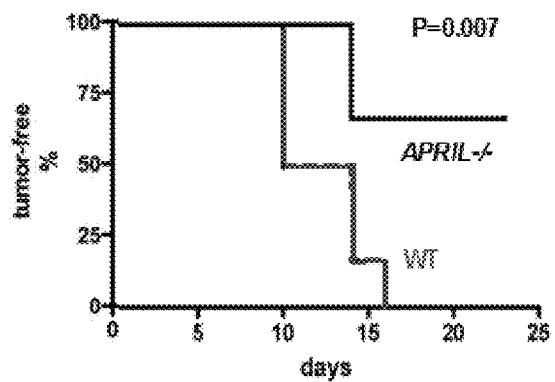

FIG. 3 represents the results of Kaplan-Meyer analysis, and statistical analysis based on a Log-rank test was performed. A p-value equal or inferior to 0.05 is considered significant.

Abscissa shows the days and the ordinate shows the percentage of tumor-free mice.

Figure 4:
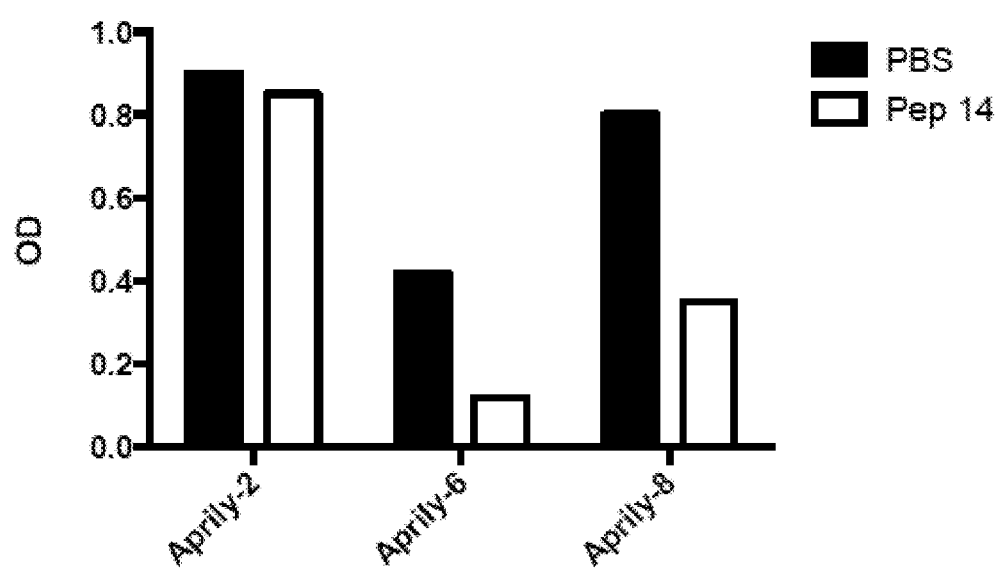

FIG. 4 represents the inhibition by peptide 14 of Aprily-2, Aprily-6 and Aprily-8 antibodies binding to coated APRIL.

Abscissa shows the tested antibodies (Aprily-2, Aprily-6 and Aprily-8) and the ordinate shows the Optical Density correlated to antibodies binding to coated APRIL. The OD is measured at 450 nm by spectrometry.

Black column represents the test with control (with PBS) and white column represents the test with peptide 14 (SEQ ID NO: 1).

Figure 5:
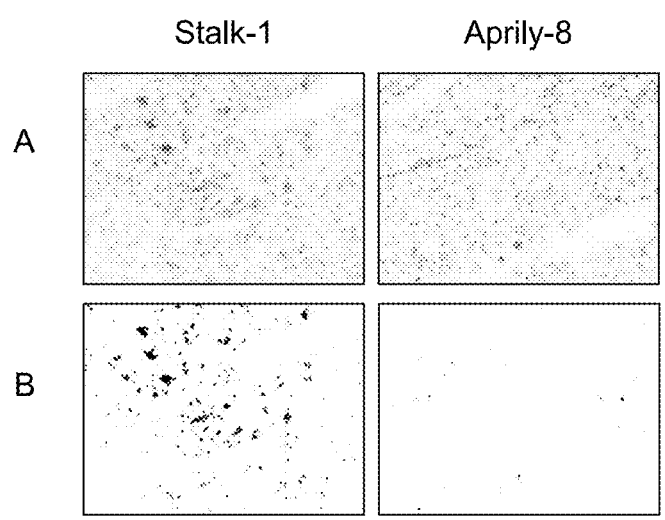

FIG. 5 represents the results of a biopsy for a DLBCL patient analyzed by Axiocam microscope, in light microscopy. The parts A and B represent the results in color and black and white, respectively.

The left panel corresponds to the immunostaining with the Stalk-1 antibody (5 µg/ml).

The right panel corresponds to the immunostaining with the antibody Aprily-8, (2 µg/ml).

Figure 6:
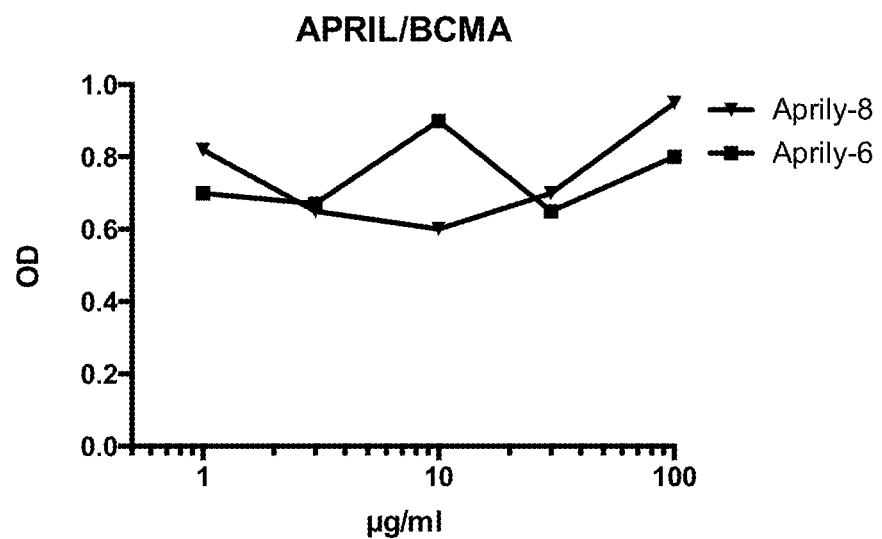
Figure 6:
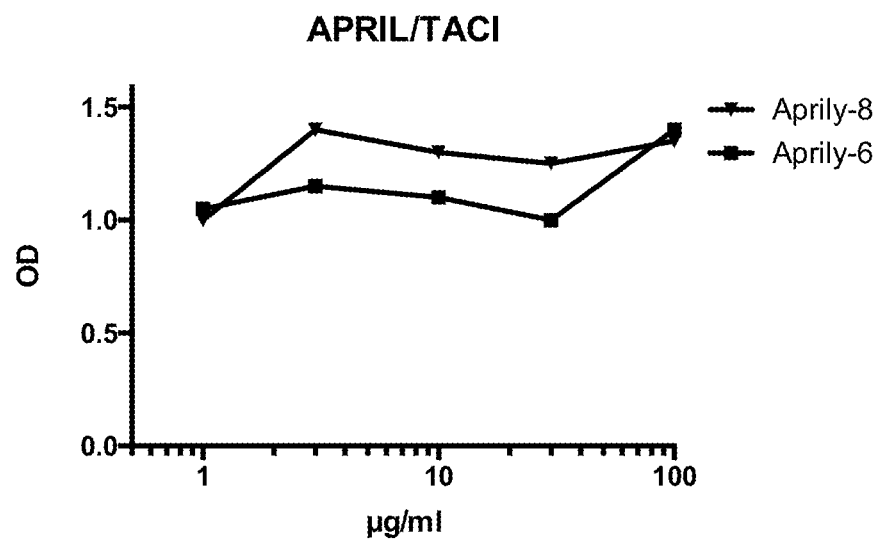

FIG. 6 represents the binding of soluble APRIL to its coated receptor BCMA or TACI in presence or Aprily-6 and Aprily-8

Part A shows the binding between APRIL and its receptor BCMA, in presence of Aprily-6 and Aprily-8. Abscissa shows the concentration of Aprily-6 or Aprily-8 and the ordinate axis shows the Optical Density correlated to the binding of APRIL to its receptor BCMA. The OD is measured at 450 nm by spectrometry.

Part B shows the binding between APRIL and its receptor TACI, in presence of Aprily-6 and Aprily-8. Abscissa shows the concentration of Aprily-6 or Aprily-8 and the ordinate axis shows the Optical Density correlated to the binding of APRIL to its receptor TACI. The OD is measured at 450 nm by spectrometry.

Figure 7:
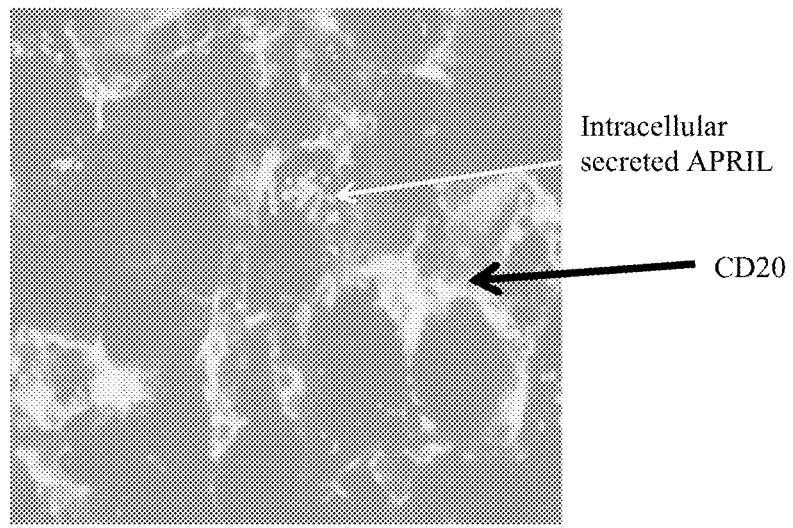

FIG. 7 represents the specific detection of APRIL inside DLBCL tumor cells. DLBCL tumor cells are stained by an anti-CD20 and secreted APRIL by Aprily-6.

EXAMPLES

Example 1: Aprily-2 Cross-reaction(s)

Immunohistochemistry
Material & Methods

Biopsies of the indicated human organs (human/mouse kidneys, human breast, and human salivary glands). were fixed, paraffin-embedded and subjected to immunostaining with control immunoglobulin (Control isotype matched Ig (mouse IgG1, 2 µg/ml), Aprily-2 (2 µg/ml, mouse IgG1 recognizing the secreted form of human APRIL), Aprily-8 (2 µg/ml, mouse IgG1 recognizing the secreted form of human APRIL), and Aprily-6 (10 µg/ml, mouse IgG1 recognizing the secreted form of human APRIL).

Tissues were washed, and incubated with a biotin-conjugated mouse Ig antiserum (available at Thermo Fisher Scientific, Inc.).

Tissues were washed, and incubated with horse raddish peroxidase (HRP)-conjugated streptavidin (available at Thermo Fisher Scientific, Inc.)

Tissue were washed and incubated with the HRP substrate amino ethyl courmarin. Light microscopy was analyzed with an Axiocam microscope (provided by Carl Zeiss).

Figure 1:
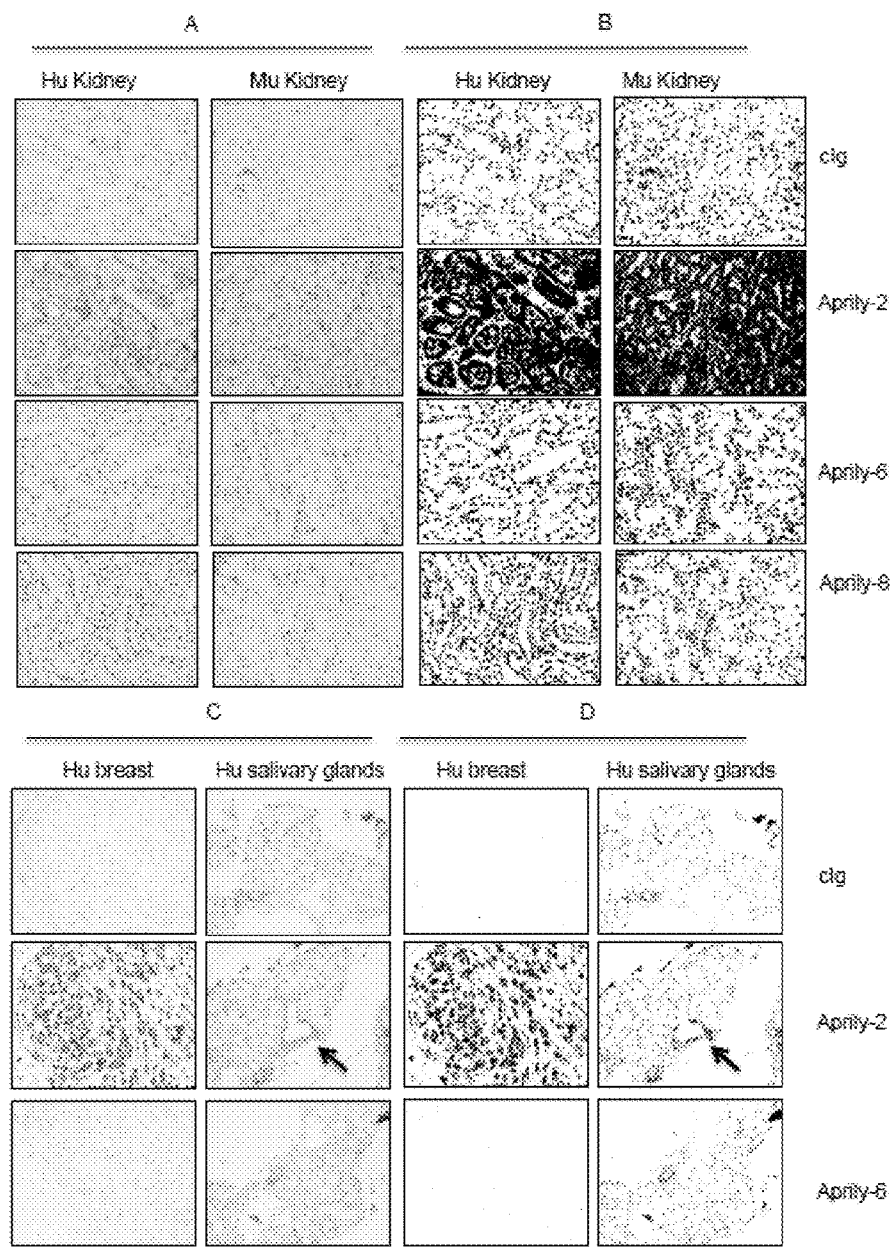
FIG. 1 represents the results of biopsy analyzed by Axiocam microscope, in light microscopy.

Pictures of the tissues are shown on FIG. 1.
Results

In human kidney, Aprily-2 gave a staining. By contrast, Aprily-6 and Aprily-8 gave no staining similar to the irrelevant control (cIg) (FIG. 1, left column).

These data indicate a differential reactivity between Aprily-2 and Aprily-6/Aprily-8.

In a kidney from APRIL−/− mice, Aprily-2 gave a staining. By contrast, Aprily-6 and Aprily-8 gave no staining similar to the irrelevant control (cIg) (FIG. 1, right column).

APRIL is obviously not present in kidneys from APRIL−/− mice, so that these data indicate a cross-reactivity of Aprily-2 with another protein not related to APRIL present in several tissues.

Thus, this proves that the use of Aprily-2 in the prognostic of B-Cell Lymphoma may give some false-positive results.

Example 2: Aprily-8 Reactivity by Itself Improves DLBCL Prognostic

Immunohistochemistry and Clinical Prospective Study
Material and Methods

Newly diagnosed DLBCL patients were recruited and treated with the actual gold 5 standard treatment, R-CHOP, according to the 38/07 protocol of the Swiss group for clinical cancer research. R-CHOP is a cocktail constituted by a monoclonal antibody, Rituximab® (Rituxan, Mab-Thera), three chemotherapeutic drugs, cyclophosphamide (C), hydroxydaunorubicine (H), oncovin (0), and one anti-inflammatory compound, prednisone (P). Details on the protocol 38/07 can be found at cancer.gov.

Biopsies from de novo DLBCL were processed and immunostained as above in example 1.

Aprily-8 (2 µg/ml, mouse IgG1 recognizing the secreted form of APRIL) and Stalk-1 (5 µg/ml, rabbit polyclonal antibody recognizing cells producing APRIL) were used. Stalk-1 has been previously described by Schwaller et al. (Schwaller, Blood, 2007).

Two pictures per biopsies were taken and quantified using the Metamorph software.

A threshold of $4.6 \cdot 10e^4$ was determined for the Metamorph quantification value. Patients were stratified according to the intensity of secreted APRIL and the number of infiltrating cells producing APRIL. Kaplan-Meyer analyses and pictures corresponding to biopsies below, equal, and above the threshold values are shown in FIG. 2. Statistical analysis was performed with a Log-rank test.
Results DLBCL patients are highly heterogeneous for the presence of APRIL-producing cells and the detection of secreted APRIL in their tumor lesions.

Different thresholds (Metamorph quantification value) were tested for the stratification of patients according to APRIL expression.

A threshold of 4.6 10e$^4$ for Aprily-8 reactivity shows that the intensity of secreted APRIL is a parameter correlating with DLBCL patient survival (FIG. 2A, left panel). By contrast none of the thresholds tested for the Stalk-1 staining correlates with patient survival (FIG. 2A, right panel).

The data shows that the intensity of secreted APRIL revealed by Aprily-8 staining is a parameter correlating with DLBCL patient survival (FIG. 2A, left panel).

The number of infiltrating cells producing APRIL revealed by Stalk-1 staining is not a parameter correlating with patient survival (FIG. 2A, right panel).

These results make APRIL detected by Aprily-8 a valuable biomarker in DLBCL prognostic. This is not the case with APRIL detected by Stalk-1.

FIG. 2B shows representative cases with the threshold value calculated at 45 Aprily-8$^+$ cells per 0.12 mm$^2$. These results make sense, since the secreted from of APRIL constitutes the active form of this molecule. These results make APRIL detected by Aprily-8 a valuable biomarker in DLBCL prognostic.

Example 3: APRIL as a Potential Predictive Biomarker in DLBCL

Mouse Xenograft Experiment
Material and Methods

5×10$^6$ cells from the human OCI-Ly7 DLBCL cell line were injected subcutaneously in immunodeficient WT and APRIL-deficient NOD-SCID mice. NOD-SCID mice were obtained from Charles River. APRIL-deficient NOD-SCID mice were obtained by backcrossing APRIL-deficient mice on a C57BL/6 background onto the immunodeficient NOD/SCID background.

OCI-Ly7 is available at DSMZ under the number ACC 688.

Tumor take was recorded by palpation. A Kaplan-Meyer analysis is shown in FIG. 3. Statistical analysis was performed with a Log-rank test.
Results The data shows that the DLBCL xenograft development is significantly impaired in subjects devoid of APRIL expression, demonstrating the DLBCL-promoting activity of APRIL. (FIG. 3).

Example 4: Epitope Mapping of Aprily-2, Aprily-6, and Aprily-8

Material and Methods

Recombinant Fc-APRIL (1 µg/ml) was coated onto the plastic surface of 96 well plates. Plates were washed and blocked with 1% BSA. Recombinant Fc-APRIL has been previously described by Ingold et al., (Ingold, Journal of Experimental Medicine, 2005).

Plates were washed and incubated with Aprily-2 (5 µg/ml), Aprily-6 (15 µg/ml), and Aprily-8 (5 µg/ml) in the absence (PBS) or presence of 10 µg/ml of peptide 14 (SEQ ID NO: 1) from human soluble APRIL.

Plates were washed and incubated with HRP-conjugated goat-anti-mouse antibody (HPR means Horse Raddish Peroxidase) (available at Thermo Fisher Scientific, Inc.).

Plates were washed and revealed with HRP substrate tetra methyl benzidine (available at Thermo Fisher Scientific, Inc.).

OD values were measured at 450 nm by spectrophotometry.

Epitope mapping of Aprily-2, Aprily-6, and Aprily-8 has also been tested with the following peptide:

Peptide 1:
(SEQ ID NO: 19)
KQKKQHSVLHLVPINATS

Peptide 2:
(SEQ ID NO: 20)
HSVLHLVPINATSKDDSD

Peptide 3:
(SEQ ID NO: 21)
LVPINATSKDDSDVTEVM

Peptide 4:
(SEQ ID NO: 22)
ATSKDDSDVTEVMWQPAL

Peptide 5:
(SEQ ID NO: 23)
DSDVTEVMWQPALRRGRG

Peptide 6:
(SEQ ID NO: 24)
EVMWQPALRRGRGLQAQG

Peptide 7:
(SEQ ID NO: 25)
PALRRGRGLQAQGYGVRI

Peptide 8:
(SEQ ID NO: 26)
GRGLQAQGYGVRIQDAGV

Peptide 9:
(SEQ ID NO: 27)
AQGYGVRIQDAGVYLLYS

Peptide 10:
(SEQ ID NO: 28)
VRIQDAGVYLLYSQVLFQ

Peptide 11:
(SEQ ID NO: 29)
AGVYLLYSQVLFQDVTFT

Peptide 12:
(SEQ ID NO: 30)
LYSQVLFQDVTFTMGQVV

Peptide 13:
(SEQ ID NO: 31)
LFQDVTFTMGQVVSREGQ

Peptide 15:
(SEQ ID NO: 32)
QVVSREGQGRQETLFRCI

Peptide 16:
(SEQ ID NO: 33)
EGQGRQETLFRCIRSMPS

Peptide 17:
(SEQ ID NO: 34)
QETLFRCIRSMPSHPDRA

Peptide 18:
(SEQ ID NO: 35)
RCIRSMPSHPDRAYNSCY

Peptide 19:
(SEQ ID NO: 36)
MPSHPDRAYNSCYSAGVF

Peptide 20:
(SEQ ID NO: 37)
DRAYNSCYSAGVFHLHQG

-continued

Peptide 21:
SCYSAGVFHLHQGDILSV
(SEQ ID NO: 38)

Peptide 22:
GVFHLHQGDILSVIIPRA
(SEQ ID NO: 39)

Peptide 23:
HQGDILSVIIPRARAKLN
(SEQ ID NO: 40)

Peptide 24:
LSVIIPRARAKLNLSPHG
(SEQ ID NO: 41)

Peptide 25:
PRARAKLNLSPHGTFLGF
(SEQ ID NO: 42)

Peptide 26:
KLNLSPHGTFLGFVKL
(SEQ ID NO: 43)

Results

The results of OD are shown in FIG. 4.

Aprily-2 and Aprily-6/Aprily-8 have different epitopes on human APRIL.

The sequence TFTMGQVVSREGQGRQET (peptide 14, SEQ ID NO: 1) includes the specific epitope recognized by Aprily-6 and Aprily-8 but not Aprily-2.

This result proves that Aprily-6/Aprily-8 also binds specifically to this sequence SEQ ID NO: 1.

The differential reactivity of Aprily-2 and Aprily-8/Aprily-6 is thus confirmed.

Example 5: Stalk-1 Identifies False-positive APRIL-high DLBCL

Material and Methods

Biopsies from de novo DLBCL were processed and immunostained as mentioned in example 1 with Aprily-8 (2 µg/ml, mouse IgG recognizing the secreted form of APRIL) and Stalk-1 (5 µg/ml, rabbit polyclonal antibody recognizing cells producing APRIL).

Results

DLBCL patients are heterogeneous for APRIL expression.

It has been previously published that the presence of infiltrating cells secreting APRIL (Stalk-1 reactivity) correlated with the detection of paracrine secreted APRIL (Aprily-8 reactivity) internalized by DLBCL tumor cells (Schwaller et al., Blood, 2007). Internalization of paracrine APRIL indicates consumption of APRIL by tumor cells. Tumor cells from these patients are likely to be dependent on APRIL for their growth.

By contrast, other patients show the presence of infiltrating cells secreting APRIL (FIG. 5, Stalk-1 reactivity, left panel) without the detection of paracrine secreted APRIL in tumor cells (FIG. 5, Aprily-8 staining, right panel). Tumor cells from these patients cannot be dependent on APRIL for their growth.

This proves that Stalk-1 identifies false-positive APRIL-high DLBCL.

Example 6: Aprily-6 and Aprily-8 do not Block the Binding of APRIL to its Receptor TACI or BCMA Material and Methods BCMA-Fc (FIG. 6A) and TACI-Fc (FIG. 6B) were coated onto 96 well plastic plates at 1 µg/ml. Wells were blocked in PBS-1% BSA, and incubated with 5 µg/ml of flag-tagged recombinant APRIL in the presence or absence of Aprily-8 and Aprily-6.

APRIL binding was detected by a biotin-conjugated anti-FLAG followed by streptavidin-HRP.

Results

It can be seen that the binding of APRIL to its receptor BCMA (FIG. 6A) or to its receptor TACI (FIG. 6B) is not modulated by the presence of the antibody Aprily-6 or Aprily-8.

This proves that Aprily-6 does not block the binding of APRIL to its receptor BCMA, nor to its receptor TACI.

This proves that Aprily-8 does not block the binding of APRIL to its receptor BCMA, nor to its receptor TACI.

Example 7: Optimization of APRIL Quantification in DLBCL

Material and Methods

DLBCL tumor cells are stained by an anti-CD20 and secreted APRIL by Aprily-6. A tumor cell using APRIL to promote its growth is a CD20+ cell with intracellular secreted APRIL.

Another quantification of APRIL can be done by specifically quantifying secreted APRIL inside tumor cells. This can be achieved with CD20 as a tumor cell marker, but also other B-cell markers including CD19, CD21 and CD22. Two-color immunofluorescence or peroxydase/phosphatase alkaline immunohistochemistry can also be done.

The invention claimed is:

1. Antibody Aprily-6 as produced by the hybridoma deposited at the Collection Nationale de Cultures de Microorganismes on Dec. 16, 2014, under the number CNCM I-4929, or an antigen-binding fragment thereof, directed against an epitope comprising or being constituted by at least six contiguous amino acids in the SEQ ID NO: 1 or a conformational epitope comprising or being constituted by at least six amino acids of SEQ ID NO: 1 which are always in the order of the said sequence, for its use for the prognosis and/or the diagnosis of a cancer.

2. Antibody or antigen-binding fragment thereof for its use for the prognosis and/or the diagnosis of a cancer according to claim 1, and wherein the said antibody is notably used without the antibody Stalk-1.

3. Antibody or antigen-binding fragment thereof for its use for the prognosis and/or the diagnosis of a cancer according to claim 1, wherein the said cancer is a lymphoma, notably chosen among all types of Hodgkin lymphomas, among the Burkitt lymphoma and Diffuse Large B-Cell Lymphoma types, or a solid tumor, such as glioblastoma or colorectal cancer.

4. Antibody or antigen-binding fragment thereof for its use for the prognosis and/or the diagnosis of a cancer according to claim 1, wherein the said diagnosis is an improved subtyping of B-Cell Lymphomas, notably for the Diffuse Large B-Cell Lymphoma types, in particular in high-risk patient.

5. Antibody or antigen-binding fragment thereof for its use for the prognosis and/or the diagnosis of a cancer according to claim 1, wherein the said prognosis is the risk assessment for patients newly diagnosed for a B-Cell Lymphoma, notably for a Diffuse Large B-Cell Lymphoma types, in particular in high-risk patient.

6. Antibody or antigen-binding fragment thereof for its use for the prognosis and/or the diagnosis of a cancer according to claim 4, wherein the high risk patient has a APRIL value above the reference threshold sample previously calculated at $4.6 \; 10^4$ according to the Metamorph microscopy automation and image analysis software, or wherein the high risk patient has a number of cells positive for secreted APRIL equal or superior to 45 positive cells per $0.12 \; mm^2$.

7. Antibody or antigen-binding fragment thereof for its use for the prognosis and/or the diagnosis of a cancer according to claim 1, wherein the said antibody is used with the antibody Aprily-2.

8. Antibody or antigen-binding fragment thereof according to claim 1, which does not block the binding of APRIL to its receptor TACI and/or BCMA.

9. Composition comprising at least the antibody or antigen-binding fragment thereof according to claim 1.

10. Hydridoma producing a monoclonal antibody Aprily-5 as deposited at the Collection Nationale de Cultures de Microorganismes on Dec. 16, 2014, under the number CNCM I-4929.

11. In vitro and/or ex vivo method for the prognosis and/or the diagnosis of a cancer, of using the antibody or antigen-binding fragment thereof according to claim 1, wherein the antibody or antigen-binding fragment is used at a concentration from 0.1 to 500 µg/ml.

12. In vitro and/or ex vivo method for the prognosis and/or the diagnosis and/or the determination of a risk assessment of a cancer, the said method using the antibody or antigen-binding fragment thereof according to claim 1, and the said method comprising the following steps:

- labeling the antibody or antigen-binging fragment thereof and using the labeled antibody or antigen-binging fragment thereof to detect in a biological sample, of a patient affected or suspected to be affected by said cancer, a number of cells positive for secreted APRIL,
- comparing the said number with the value of 45 positive cells for secreted APRIL per $0.12 \; mm^2$,
- deducing from said comparison whether the said patient may be expected to be suffering from a cancer.

* * * * *

SEQUENCE LISTING

<160> NUMBER OF SEQ ID NOS: 48

<210> SEQ ID NO 1
<211> LENGTH: 18
<212> TYPE: PRT
<213> ORGANISM: Artificial sequence
<220> FEATURE:
<223> OTHER INFORMATION: Fragment of the APRIL protein (contiguous amino acids)

<400> SEQUENCE: 1

Thr Phe Thr Met Gly Gln Val Val Ser Arg Glu Gly Gln Gly Arg Gln
1               5                   10                  15

Glu Thr

<210> SEQ ID NO 2
<211> LENGTH: 6
<212> TYPE: PRT
<213> ORGANISM: Artificial sequence
<220> FEATURE:
<223> OTHER INFORMATION: Fragment of the APRIL protein (contiguous amino acids)

<400> SEQUENCE: 2

Thr Phe Thr Met Gly Gln
1               5

<210> SEQ ID NO 3
<211> LENGTH: 6
<212> TYPE: PRT
<213> ORGANISM: Artificial sequence
<220> FEATURE:
<223> OTHER INFORMATION: Fragment of the APRIL protein (contiguous amino acids)

<400> SEQUENCE: 3

Phe Thr Met Gly Gln Val
1               5

<210> SEQ ID NO 4
<211> LENGTH: 6
<212> TYPE: PRT
<213> ORGANISM: Artificial sequence
<220> FEATURE:
<223> OTHER INFORMATION: Fragment of the APRIL protein (contiguous amino acids)

<400> SEQUENCE: 4

Thr Met Gly Gln Val Val
1               5

<210> SEQ ID NO 5
<211> LENGTH: 6
<212> TYPE: PRT
<213> ORGANISM: Artificial sequence
<220> FEATURE:
<223> OTHER INFORMATION: Fragment of the APRIL protein (contiguous amino acids)

<400> SEQUENCE: 5

Met Gly Gln Val Val Ser
1               5

<210> SEQ ID NO 6
<211> LENGTH: 6
<212> TYPE: PRT
<213> ORGANISM: Artificial sequence
<220> FEATURE:
<223> OTHER INFORMATION: Fragment of the APRIL protein (contiguous amino acids)

<400> SEQUENCE: 6

Gly Gln Val Val Ser Arg
1               5

<210> SEQ ID NO 7
<211> LENGTH: 6
<212> TYPE: PRT
<213> ORGANISM: Artificial sequence
<220> FEATURE:
<223> OTHER INFORMATION: Fragment of the APRIL protein (contiguous amino acids)

```
<400> SEQUENCE: 7

Gln Val Val Ser Arg Glu
1               5

<210> SEQ ID NO 8
<211> LENGTH: 6
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 8

Val Val Ser Arg Glu Gly
1               5

<210> SEQ ID NO 9
<211> LENGTH: 6
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 9

Val Ser Arg Glu Gly Gln
1               5

<210> SEQ ID NO 10
<211> LENGTH: 6
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 10

Ser Arg Glu Gly Gln Gly
1               5

<210> SEQ ID NO 11
<211> LENGTH: 6
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 11

Arg Glu Gly Gln Gly Arg
1               5

<210> SEQ ID NO 12
<211> LENGTH: 6
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 12

Glu Gly Gln Gly Arg Gln
1               5

<210> SEQ ID NO 13
<211> LENGTH: 6
<212> TYPE: PRT
```

```
<213> ORGANISM: Artificial sequence
<220> FEATURE:
<223> OTHER INFORMATION: Fragment of the APRIL protein (contiguous amino
      acids)

<400> SEQUENCE: 13

Gly Gln Gly Arg Gln Glu
1               5

<210> SEQ ID NO 14
<211> LENGTH: 6
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 14

Gln Gly Arg Gln Glu Thr
1               5

<210> SEQ ID NO 15
<211> LENGTH: 13
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 15

Gly Thr Gly Gly Pro Ser Gln Asn Gly Glu Gly Tyr Pro
1               5                   10

<210> SEQ ID NO 16
<211> LENGTH: 233
<212> TYPE: PRT
<213> ORGANISM: Homo Sapiens

<400> SEQUENCE: 16

Met Gly Gly Pro Val Arg Glu Pro Ala Leu Ser Val Ala Leu Trp Leu
1               5                   10                  15

Ser Trp Gly Ala Ala Leu Gly Ala Val Ala Cys Ala Met Ala Leu Leu
                20                  25                  30

Thr Gln Gln Thr Glu Leu Gln Ser Leu Arg Arg Glu Val Ser Arg Leu
        35                  40                  45

Gln Gly Thr Gly Gly Pro Ser Gln Asn Gly Glu Gly Tyr Pro Trp Gln
    50                  55                  60

Ser Leu Pro Glu Gln Ser Ser Asp Ala Leu Glu Ala Trp Glu Asn Gly
65                  70                  75                  80

Glu Arg Ser Arg Lys Arg Arg Ala Val Leu Thr Gln Lys Gln Lys Lys
                85                  90                  95

Gln His Ser Val Leu His Leu Val Pro Ile Asn Ala Thr Ser Lys Asp
            100                 105                 110

Asp Ser Asp Val Thr Glu Val Met Trp Gln Pro Ala Leu Arg Arg Gly
        115                 120                 125

Arg Gly Leu Gln Ala Gln Gly Tyr Gly Val Arg Ile Gln Asp Ala Gly
    130                 135                 140

Val Tyr Leu Leu Tyr Ser Gln Val Leu Phe Gln Asp Val Thr Phe Thr
145                 150                 155                 160

Met Gly Gln Val Val Ser Arg Glu Gly Gln Gly Arg Gln Glu Thr Leu
                165                 170                 175
```

```
Phe Arg Cys Ile Arg Ser Met Pro Ser His Pro Asp Arg Ala Tyr Asn
            180                 185                 190

Ser Cys Tyr Ser Ala Gly Val Phe His Leu His Gln Gly Asp Ile Leu
        195                 200                 205

Ser Val Ile Ile Pro Arg Ala Arg Ala Lys Leu Asn Leu Ser Pro His
    210                 215                 220

Gly Thr Phe Leu Gly Phe Val Lys Leu
225                 230

<210> SEQ ID NO 17
<211> LENGTH: 8
<212> TYPE: PRT
<213> ORGANISM: Artificial sequence
<220> FEATURE:
<223> OTHER INFORMATION: Fragment of the APRIL protein (non-contiguous
      amino acids)

<400> SEQUENCE: 17

Thr Phe Met Ser Gly Gln Glu Thr
1               5

<210> SEQ ID NO 18
<211> LENGTH: 7
<212> TYPE: PRT
<213> ORGANISM: Artificial sequence
<220> FEATURE:
<223> OTHER INFORMATION: Fragment of the APRIL protein (non-contiguous
      amino acids)

<400> SEQUENCE: 18

Thr Phe Gly Glu Gln Val Val
1               5

<210> SEQ ID NO 19
<211> LENGTH: 18
<212> TYPE: PRT
<213> ORGANISM: Artificial sequence
<220> FEATURE:
<223> OTHER INFORMATION: Fragment of the APRIL protein (contiguous
      amino acids)

<400> SEQUENCE: 19

Lys Gln Lys Lys Gln His Ser Val Leu His Leu Val Pro Ile Asn Ala
1               5                   10                  15

Thr Ser

<210> SEQ ID NO 20
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 20

His Ser Val Leu His Leu Val Pro Ile Asn Ala Thr Ser Lys Asp Asp
1               5                   10                  15

Ser Asp

<210> SEQ ID NO 21
<211> LENGTH: 18
<212> TYPE: PRT
<213> ORGANISM: Artificial sequence
<220> FEATURE:
<223> OTHER INFORMATION: Fragment of the APRIL protein (contiguous amino
```

-continued acids)

<400> SEQUENCE: 21

Leu Val Pro Ile Asn Ala Thr Ser Lys Asp Asp Ser Asp Val Thr Glu
1               5                   10                  15

Val Met

<210> SEQ ID NO 22
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 22

Ala Thr Ser Lys Asp Asp Ser Asp Val Thr Glu Val Met Trp Gln Pro
1               5                   10                  15

Ala Leu

<210> SEQ ID NO 23
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 23

Asp Ser Asp Val Thr Glu Val Met Trp Gln Pro Ala Leu Arg Arg Gly
1               5                   10                  15

Arg Gly

<210> SEQ ID NO 24
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 24

Glu Val Met Trp Gln Pro Ala Leu Arg Arg Gly Arg Gly Leu Gln Ala
1               5                   10                  15

Gln Gly

<210> SEQ ID NO 25
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 25

Pro Ala Leu Arg Arg Gly Arg Gly Leu Gln Ala Gln Gly Tyr Gly Val
1               5                   10                  15

Arg Ile

<210> SEQ ID NO 26
<211> LENGTH: 18
<212> TYPE: PRT
<213> ORGANISM: Artificial sequence
<220> FEATURE:

<223> OTHER INFORMATION: Fragment of the APRIL protein (contiguous amino
      acids)

<400> SEQUENCE: 26

Gly Arg Gly Leu Gln Ala Gln Gly Tyr Gly Val Arg Ile Gln Asp Ala
1               5                   10                  15

Gly Val

<210> SEQ ID NO 27
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 27

Ala Gln Gly Tyr Gly Val Arg Ile Gln Asp Ala Gly Val Tyr Leu Leu
1               5                   10                  15

Tyr Ser

<210> SEQ ID NO 28
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 28

Val Arg Ile Gln Asp Ala Gly Val Tyr Leu Leu Tyr Ser Gln Val Leu
1               5                   10                  15

Phe Gln

<210> SEQ ID NO 29
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 29

Ala Gly Val Tyr Leu Leu Tyr Ser Gln Val Leu Phe Gln Asp Val Thr
1               5                   10                  15

Phe Thr

<210> SEQ ID NO 30
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 30

Leu Tyr Ser Gln Val Leu Phe Gln Asp Val Thr Phe Thr Met Gly Gln
1               5                   10                  15

Val Val

<210> SEQ ID NO 31
<211> LENGTH: 18
<212> TYPE: PRT
<213> ORGANISM: Artificial sequence -continued

```
<220> FEATURE:
<223> OTHER INFORMATION: Fragment of the APRIL protein (contiguous amino
      acids)

<400> SEQUENCE: 31

Leu Phe Gln Asp Val Thr Phe Thr Met Gly Gln Val Val Ser Arg Glu
1               5                   10                  15

Gly Gln

<210> SEQ ID NO 32
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 32

Gln Val Val Ser Arg Glu Gly Gln Gly Arg Gln Glu Thr Leu Phe Arg
1               5                   10                  15

Cys Ile

<210> SEQ ID NO 33
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 33

Glu Gly Gln Gly Arg Gln Glu Thr Leu Phe Arg Cys Ile Arg Ser Met
1               5                   10                  15

Pro Ser

<210> SEQ ID NO 34
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 34

Gln Glu Thr Leu Phe Arg Cys Ile Arg Ser Met Pro Ser His Pro Asp
1               5                   10                  15

Arg Ala

<210> SEQ ID NO 35
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 35

Arg Cys Ile Arg Ser Met Pro Ser His Pro Asp Arg Ala Tyr Asn Ser
1               5                   10                  15

Cys Tyr

<210> SEQ ID NO 36
<211> LENGTH: 18
<212> TYPE: PRT
```

```
<213> ORGANISM: Artificial sequence
<220> FEATURE:
<223> OTHER INFORMATION: Fragment of the APRIL protein (contiguous amino
      acids)

<400> SEQUENCE: 36

Met Pro Ser His Pro Asp Arg Ala Tyr Asn Ser Cys Tyr Ser Ala Gly
1               5                   10                  15

Val Phe

<210> SEQ ID NO 37
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 37

Asp Arg Ala Tyr Asn Ser Cys Tyr Ser Ala Gly Val Phe His Leu His
1               5                   10                  15

Gln Gly

<210> SEQ ID NO 38
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 38

Ser Cys Tyr Ser Ala Gly Val Phe His Leu His Gln Gly Asp Ile Leu
1               5                   10                  15

Ser Val

<210> SEQ ID NO 39
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 39

Gly Val Phe His Leu His Gln Gly Asp Ile Leu Ser Val Ile Ile Pro
1               5                   10                  15

Arg Ala

<210> SEQ ID NO 40
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 40

His Gln Gly Asp Ile Leu Ser Val Ile Ile Pro Arg Ala Arg Ala Lys
1               5                   10                  15

Leu Asn

<210> SEQ ID NO 41
<211> LENGTH: 18
```

```
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 41

Leu Ser Val Ile Ile Pro Arg Ala Arg Ala Lys Leu Asn Leu Ser Pro
1               5                   10                  15

His Gly

<210> SEQ ID NO 42
<211> LENGTH: 18
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 42

Pro Arg Ala Arg Ala Lys Leu Asn Leu Ser Pro His Gly Thr Phe Leu
1               5                   10                  15

Gly Phe

<210> SEQ ID NO 43
<211> LENGTH: 16
<212> TYPE: PRT
<213> ORGANISM: Artificial sequence
<220> FEATURE:
<223> OTHER INFORMATION: Fragment of the APRIL protein (contiguous amino
      acids)

<400> SEQUENCE: 43

Lys Leu Asn Leu Ser Pro His Gly Thr Phe Leu Gly Phe Val Lys Leu
1               5                   10                  15

<210> SEQ ID NO 44
<211> LENGTH: 9
<212> TYPE: PRT
<213> ORGANISM: Artificial Sequence
<220> FEATURE:
<223> OTHER INFORMATION: Fragment of the APRIL protein

<400> SEQUENCE: 44

Val Ser Arg Glu Gly Gln Gly Arg Gln
1               5

<210> SEQ ID NO 45
<211> LENGTH: 6
<212> TYPE: PRT
<213> ORGANISM: Artificial Sequence
<220> FEATURE:
<223> OTHER INFORMATION: Fragment of the APRIL protein

<400> SEQUENCE: 45

Ser Met Pro Ser His Pro
1               5

<210> SEQ ID NO 46
<211> LENGTH: 4
<212> TYPE: PRT
<213> ORGANISM: Artificial Sequence
<220> FEATURE:
<223> OTHER INFORMATION: Fragment of the APRIL protein

<400> SEQUENCE: 46
```

```
Thr Leu Phe Arg
1

<210> SEQ ID NO 47
<211> LENGTH: 9
<212> TYPE: PRT
<213> ORGANISM: Artificial Sequence
<220> FEATURE:
<223> OTHER INFORMATION: Fragment of the APRIL protein

<400> SEQUENCE: 47

Gln Asp Val Thr Phe Thr Met Gly Gln
1               5

<210> SEQ ID NO 48
<211> LENGTH: 11
<212> TYPE: PRT
<213> ORGANISM: Artificial Sequence
<220> FEATURE:
<223> OTHER INFORMATION: Fragment of the APRIL protein

<400> SEQUENCE: 48

Ile Arg Ser Met Pro Ser His Pro Asp Arg Ala
1               5                   10
```